United States Patent
Shiraishi

(10) Patent No.: US 12,061,326 B2
(45) Date of Patent: Aug. 13, 2024

(54) OBSERVATION DEVICE, OBSERVATION METHOD, AND OBSERVATION DEVICE CONTROL PROGRAM

(71) Applicant: FUJIFILM Corporation, Tokyo (JP)

(72) Inventor: Yasushi Shiraishi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 703 days.

(21) Appl. No.: 17/202,821

(22) Filed: Mar. 16, 2021

(65) Prior Publication Data

US 2021/0199941 A1    Jul. 1, 2021

Related U.S. Application Data

(63) Continuation of application No. PCT/JP2019/034680, filed on Sep. 4, 2019.

(30) Foreign Application Priority Data

Sep. 27, 2018  (JP) ................................. 2018-182731

(51) Int. Cl.
| | |
|---|---|
| *G02B 21/24* | (2006.01) |
| *C12M 1/34* | (2006.01) |
| *G02B 7/28* | (2021.01) |
| *G02B 21/00* | (2006.01) |
| *G02B 21/26* | (2006.01) |

(Continued)

(52) U.S. Cl.
CPC .......... *G02B 21/0024* (2013.01); *C12M 1/34* (2013.01); *G02B 7/28* (2013.01); *G02B 21/26* (2013.01); *G02B 21/34* (2013.01); *G02B 21/365* (2013.01)

(58) Field of Classification Search
CPC .................................................. G02B 21/0024
See application file for complete search history.

(56) References Cited

U.S. PATENT DOCUMENTS 6,042,475 A * 3/2000 Darden ................ F24F 11/0001
                                                160/202
6,043,475 A    3/2000 Shimada et al.
(Continued)

FOREIGN PATENT DOCUMENTS

| JP | 2007-248086 A | 9/2007 |
| JP | 2008-256927 A | 10/2008 |

(Continued)

OTHER PUBLICATIONS

Extended European Search Report for European Application No. 19864144.1, dated Oct. 21, 2021.

(Continued)

*Primary Examiner* — Daniel T Tekle
(74) *Attorney, Agent, or Firm* — Birch, Stewart, Kolasch & Birch, LLP

(57) ABSTRACT

A detection section detects a position of a container in a vertical direction, and an imaging optical system controller acquires an adjustment value of an imaging position of an imaging optical system according to the detected position. A correction section corrects the adjustment value according to a change in a refractive index of the container according to a temperature of the container. The imaging optical system controller adjusts an imaging position of an observation target on the basis of the corrected adjustment value.

15 Claims, 12 Drawing Sheets

(51) Int. Cl.
    *G02B 21/34*     (2006.01)
    *G02B 21/36*     (2006.01)

(56) References Cited

U.S. PATENT DOCUMENTS

| | | | |
|---|---|---|---|
| 6,137,640 A * | 10/2000 | Viola | G02B 7/28 |
| | | | 355/53 |
| 2003/0184855 A1 | 10/2003 | Yasuda et al. | |
| 2007/0216896 A1 | 9/2007 | Chikamatsu et al. | |
| 2008/0247038 A1 | 10/2008 | Sasaki et al. | |
| 2014/0240700 A1 | 8/2014 | Ogawa et al. | |
| 2019/0072749 A1 | 3/2019 | Wakui | |
| 2019/0212539 A1 | 7/2019 | Shiraishi | |

FOREIGN PATENT DOCUMENTS

| | | |
|---|---|---|
| JP | 2014-194521 A | 10/2014 |
| JP | 2017-207567 A | 11/2017 |
| WO | WO 2017/199537 A1 | 11/2017 |
| WO | WO 2018/061756 A1 | 4/2018 |

OTHER PUBLICATIONS

International Preliminary Report on Patentability and Written Opinion of the International Searching Authority for International Application No. PCT/JP2019/034680, dated Apr. 8, 2021, with an English translation.
International Search Report for International Application No. PCT/JP2019/034680, dated Oct. 8, 2019, with an English translation.

* cited by examiner

FIG. 1
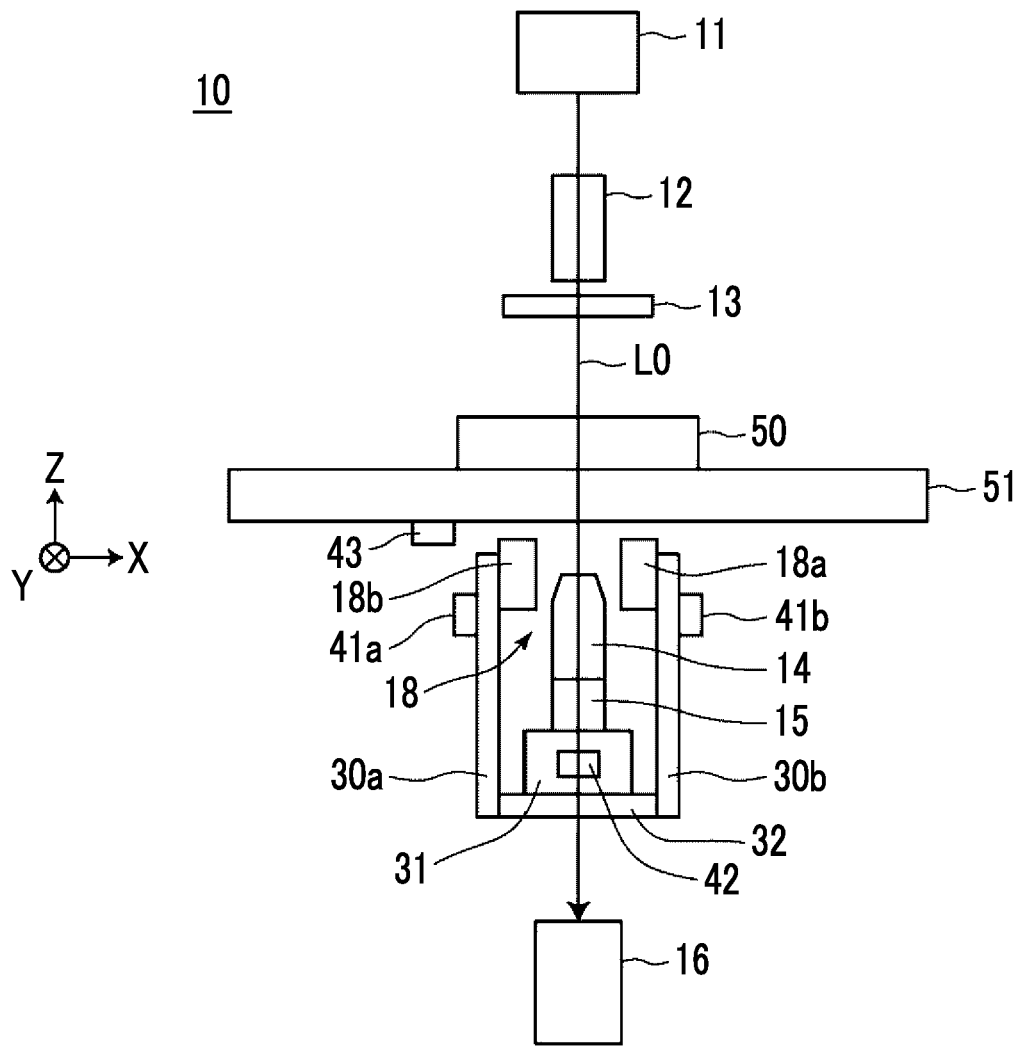
FIG. 2
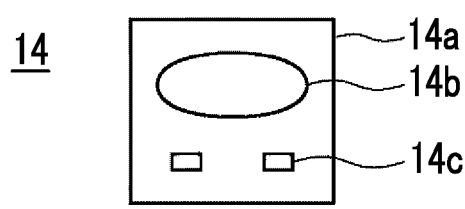
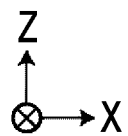

MOVEMENT DIRECTION (FORWARD)

MOVEMENT DIRECTION (BACKWARD)

OBSERVATION DEVICE, OBSERVATION METHOD, AND OBSERVATION DEVICE CONTROL PROGRAM

CROSS-REFERENCE TO RELATED APPLICATIONS

This application is a Continuation of PCT International Application No. PCT/JP2019/034680 filed on Sep. 4, 2019, which claims priority under 35 U.S.C § 119(a) to Japanese Patent Application No. 2018-182731 filed on Sep. 27, 2018. Each of the above application(s) is hereby expressly incorporated by reference, in its entirety, into the present application.

BACKGROUND OF THE INVENTION

1. Field of the Invention

The present disclosure relates to an observation device, an observation method, and an observation device control program for observing an entire image of an observation target by relatively moving a container in which the observation target is contained and an imaging optical system that forms an image of the observation target.

2. Description of the Related Art

In the related art, a technique for imaging a multipotential stem cell such as an embryonic stem (ES) cell or an induced pluripotent stem (iPS) cell, a differentiated and induced cell, or the like using an observation device such as a microscope, and capturing a feature of the image to decide a differentiation state of the cell, or the like has been proposed.

The multipotential stem cell such as an ES cell or an iPS cell is able to be differentiated into cells of various tissues, and may be applied to regenerative medicine, development of medicines, explanation of diseases, or the like.

On the other hand, in a case where a cell is imaged using a microscope as described above, in order to acquire a high-magnification wide view image, for example, a so-called tiling imaging for scanning the inside of a range of a culture container such as a well plate using an observation region of an imaging optical system and capturing an image for each observation region, and then, combining the images at the respective observation regions has been proposed.

In a case where such tiling imaging is performed, it is necessary to perform an auto-focus control for adjusting a focal position of the imaging optical system for each observation region. A technique for performing the auto-focus control at high speed has been proposed. For example, JP2017-207567A has proposed a technique for performing tiling imaging using an imaging optical system while moving a stage on which a container is installed in a main scanning direction and a sub-scanning direction. In the technique disclosed in JP2017-207567A, a position of the container in a vertical direction at a forward position in a movement direction of an observation region of the imaging optical system with reference to a position of the observation region with respect to the container is detected using a displacement sensor, an objective lens is moved in an optical axis direction using a piezoelectric element or the like on the basis of the detected position of the container in the vertical direction, so that an auto-focus control is performed. Thus, in the technique disclosed in JP2017-207567A, it is possible to perform the auto-focus control at high speed.

However, a temperature control is important in culturing cells. Accordingly, in an observation device, a container is imaged in an environment where the temperature is controlled. However, it takes time from the start of temperature adjustment to stabilization of the temperature in the observation device. Here, an objective lens and a displacement sensor are supported on a base of the device by a metallic support member such as aluminum or brass. The metallic support member expands and contracts with a change in temperature. Accordingly, the position of the objective lens and the position of the displacement sensor are changed between the start of the temperature adjustment and the stabilization of the temperature and thereafter.

Since a structure of cells is very small, it is necessary to adjust a focal position in the unit of submicron in imaging cells using an observation device. However, in a case where the position of the objective lens and the position of the displacement sensor are changed due to temperature change, it is not possible to accurately adjust the focal position. Accordingly, in a device that observes a sample such as cells, a technique for measuring a temperature and correcting a focal position of an objective lens in consideration of a fluctuation of the focal position of the objective lens and a fluctuation of a displacement sensor according to the measured temperature has been proposed (see JP2014-194521A, JP2007-248086A, and JP2008-256927A). Since an auto-focus control can be performed accurately regardless of a change in an ambient temperature using the techniques disclosed in JP2014-194521A, JP2007-248086A, and JP2008-256927A, it is possible to acquire an image with reduced blur.

SUMMARY OF THE INVENTION

In this regard, the objective lens is driven so that the focal position is aligned with a bottom portion of a well in a culture container such as a well plate, that is, an interface between an observation target and the well. Here, in many cases, the culture container such as a well plate is made of resin. A refractive index of the resin changes with a change in temperature.

In a case where the refractive index of the container changes in this way, an imaging position of light passed through the container is changed. Thus, even in a case where the focal position of the objective lens is corrected according to the measured temperature, the corrected focal position and the position of the bottom portion of the well in the container deviate from each other, and as a result, there occurs a problem that the captured image is blurred.

The present disclosure has been made in view of the above circumstances, and an object of the present disclosure is to provide a technique for acquiring an image with reduced blur even in a case where an ambient temperature changes.

According to an aspect of the present disclosure, there is provided an observation device including: an imaging optical system that forms an image of an observation target contained in a transparent container;
 a horizontal driving section that moves at least one of the container or the imaging optical system in a horizontal plane;
 a scanning controller that controls the horizontal driving section to move an observation region of the imaging optical system and to scan the container;
 a detection section that has at least one displacement sensor detecting a position of the container in a vertical direction, and detects the position of the container in the vertical direction at a position in front of a position of the observation region of the imaging optical system with respect to the container in a movement direction of the observation region;

an imaging position adjustment section that adjusts an imaging position of the image of the observation target on the basis of an adjustment value according to the position of the container in the vertical direction detected by the detection section;

a first temperature measuring section that measures a temperature of a support member that supports the detection section as a first temperature;

a second temperature measuring section that measures a temperature of a support member that supports the imaging optical system as a second temperature;

a third temperature measuring section that measures a temperature of the container as a third temperature; and a correction section that corrects the adjustment value on the basis of a refractive index of the container according to the first temperature, the second temperature, and the third temperature, in which the imaging position adjustment section adjusts the imaging position of the image of the observation target on the basis of the corrected adjustment value.

Here, the "transparent" in the present disclosure does not include only transmitting light in all wavelength ranges, but also includes transmitting light in a specific wavelength range. Further, a light source may be arbitrarily selected depending on measurement conditions, and a light source including a plurality of wavelengths such as a white light source may be used, or a monochromatic light source having only a specific wavelength range may be used. Further, moving at least one of the container or the imaging optical system in the "horizontal plane" mentioned above means relatively moving the container and the imaging optical system while maintaining a constant separation distance between the container and the imaging optical system. Further, the "vertical direction of the container" mentioned above refers to a normal direction in the horizontal plane of the container.

In the observation device according to the present disclosure, the detection section may switch a position of the displacement sensor or the displacement sensor to be used according to a change in the movement direction of the observation region.

Further, in the observation device according to the present disclosure, the container may be a well plate having a plurality of wells, the third temperature measuring section may measure a temperature of each of the plurality of wells, and the correction section may correct the adjustment value according to each of the plurality of wells.

Further, in the observation device according to the present disclosure, the imaging optical system may include an objective lens that forms the image of the observation target in the container, the imaging position adjustment section may adjust the imaging position of the image of the observation target by adjusting a position of the objective lens in the vertical direction, and the second temperature measuring section may measure a temperature of a support member that supports the imaging position adjustment section.

Further, in the observation device according to the present disclosure, the correction section may correct the adjustment value on the basis of a temperature difference between the first temperature and the second temperature.

Further, in the observation device according to the present disclosure, the correction section may derive, with reference to a first lookup table that defines a relationship between the first temperature and a first correction coefficient for correcting the adjustment value, a second lookup table that defines a relationship between the second temperature and a second correction coefficient for correcting the adjustment value, and a third lookup table that defines a relationship between the third temperature and a third correction coefficient for correcting the adjustment value in consideration of the refractive index of the container according to the third temperature, the first correction coefficient, the second correction coefficient, and the third correction coefficient, and may correct the adjustment value by using the first correction coefficient, the second correction coefficient, and the third correction coefficient.

Further, according to another aspect of the present disclosure, there is provided an observation method for moving at least one of a transparent container in which an observation target is contained or an imaging optical system that forms an image of the observation target in the container in a horizontal plane and capturing the image of the observation target formed by the imaging optical system using an imaging element, the method including:

a step of including at least one displacement sensor detecting a position of the container in a vertical direction, and detecting the position of the container in the vertical direction at a position in front of a position of the observation region of the imaging optical system with respect to the container in a movement direction of the observation region, by a detection section that detects the position of the container in the vertical direction;

a step of adjusting an imaging position of the image of the observation target on the basis of an adjustment value according to the position of the container in the vertical direction detected by the detection section;

a step of measuring a temperature of a support member that supports the detection section as a first temperature;

a step of measuring a temperature of a support member that supports the imaging optical system as a second temperature;

a step of measuring a temperature of the container as a third temperature; and a step of correcting the adjustment value on the basis of a refractive index of the container according to the first temperature, the second temperature, and the third temperature, in which in the step of adjusting the imaging position, the imaging position of the image of the observation target is adjusted by the corrected adjustment value.

According to still another aspect of the present disclosure, there is provided an observation device control program causing a computer to execute a procedure of moving at least one of a transparent container in which an observation target is contained or an imaging optical system that forms an image of the observation target in the container in a horizontal plane and capturing the image of the observation target formed by the imaging optical system using an imaging element, the program causing the computer to execute:

a procedure of including at least one displacement sensor detecting a position of the container in a vertical direction, and detecting the position of the container in the vertical direction at a position in front of a position of the observation region of the imaging optical system with respect to the container in a movement direction of the observation region, by a detection section that detects the position of the container in the vertical direction;

a procedure of adjusting an imaging position of the image of the observation target on the basis of an adjustment value according to the position of the container in the vertical direction detected by the detection section;

a procedure of measuring a temperature of a support member that supports the detection section as a first temperature;

a procedure of measuring a temperature of a support member that supports the imaging optical system as a second temperature;

a procedure of measuring a temperature of the container as a third temperature; and a procedure of correcting the adjustment value on the basis of a refractive index of the container according to the first temperature, the second temperature, and the third temperature, in which in the procedure of adjusting the imaging position, the imaging position of the image of the observation target is adjusted by the corrected adjustment value.

According to still another aspect of the present disclosure, there is provided an observation device including: a memory that stores a command to be executed by a computer; and a processor configured to execute the stored command, in which the processor executes, in moving at least one of a transparent container in which an observation target is contained or an imaging optical system that forms an image of the observation target in the container in a horizontal plane and capturing the image of the observation target formed by the imaging optical system using an imaging element, a step of including at least one displacement sensor detecting a position of the container in a vertical direction, and detecting the position of the container in the vertical direction at a position in front of a position of the observation region of the imaging optical system with respect to the container in a movement direction of the observation region, by a detection section that detects the position of the container in the vertical direction;

a step of adjusting an imaging position of the image of the observation target on the basis of an adjustment value according to the position of the container in the vertical direction detected by the detection section;

a step of measuring a temperature of a support member that supports the detection section as a first temperature;

a step of measuring a temperature of a support member that supports the imaging optical system as a second temperature;

a step of measuring a temperature of the container as a third temperature; and a step of correcting the adjustment value on the basis of a refractive index of the container according to the first temperature, the second temperature, and the third temperature, in which in the step of adjusting the imaging position, the imaging position of the image of the observation target is adjusted by the corrected adjustment value.

According to the present disclosure, it is possible to acquire an image with reduced blur even in a case where the ambient temperature is changed.

BRIEF DESCRIPTION OF THE DRAWINGS

FIG. 1 is a diagram showing a schematic configuration of a microscope observation system that uses an observation device according to an embodiment of the present disclosure.

FIG. 2 is a schematic diagram showing a configuration of an imaging optical system.

DESCRIPTION OF THE PREFERRED EMBODIMENTS

Figure 3:
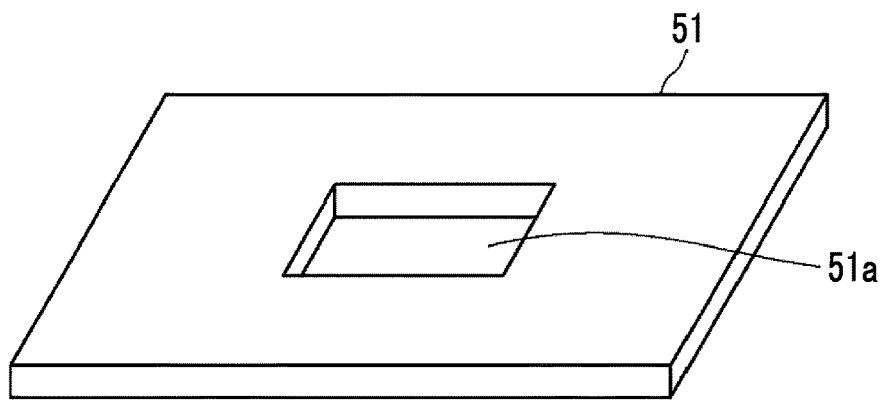
FIG. 3 is a perspective view showing a configuration of a stage.

Hereinafter, a microscope observation system that uses an observation device, an observation method, and an observation device control program according to embodiments of the present disclosure will be described in detail with reference to the accompanying drawings. FIG. 1 is a block diagram showing a schematic configuration of a microscope device 10 in a microscope observation system of the embodiment.

The microscope device 10 captures a phase difference image of a cultivated cell that is an observation target. Specifically, as shown in FIG. 1, the microscope device 10 comprises a white light source 11 that emits white light, a condenser lens 12, a slit plate 13, an imaging optical system 14, an imaging position adjustment section 15, an imaging element 16, and a detection section 18.

The slit plate 13 has a configuration in which a ring-shaped slit through which white light passes is formed in a light screen that shields white light emitted from the white light source 11, in which a ring-shaped illumination light L0 is formed as the white light passes through the slit.

FIG. 2 is a diagram showing a detailed configuration of the imaging optical system 14. The imaging optical system 14 includes a phase difference lens 14a and an imaging lens 14d, as shown in FIG. 2. The phase difference lens 14a includes an objective lens 14b and a phase plate 14c. The phase plate 14c has a configuration in which a phase ring is formed in a transparent plate that is transparent with respect to a wavelength of the illumination light L0. The size of the above-described slit plate 13 is in a cooperative relation with the phase ring of the phase plate 14c.

The phase ring has a configuration in which a phase membrane that shifts a phase of incident light by ¼ of a wavelength and a dimmer filter that dims incident light are formed in a ring shape. The phase of direct light incident onto the phase ring shifts by ¼ of a wavelength after passing through the phase ring, and thus, its brightness is weakened. On the other hand, most of diffracted light diffracted by an observation target passes through the transparent plate of the phase plate 14c, and thus, its phase and brightness are not changed.

The phase difference lens 14a having the objective lens 14b is moved in an optical axis direction of the objective lens 14b by the imaging position adjustment section 15 shown in FIG. 1. In this embodiment, the optical axis direction of the objective lens 14b and a Z direction (vertical direction) are the same directions. As the objective lens 14b is moved in the Z direction, an auto-focus control is performed, and contrast of a phase difference image captured by the imaging element 16 is adjusted.

The imaging element 16 captures a phase difference image formed by the imaging optical system 14. As the imaging element 16, a charge-coupled device (CCD) image sensor, a complementary metal-oxide semiconductor (CMOS) image sensor, or the like may be used. As the imaging element, an imaging element in which color filters of red, green, and blue (R, G, and B) are provided may be used, or a monochromic imaging element may be used.

The detection section 18 detects a position of the culture container 50 in a Z direction (vertical direction), installed on the stage 51. The detection section 18 includes a first displacement sensor 18a and a second displacement sensor 18b. The first displacement sensor 18a and the second displacement sensor 18b are provided in parallel in the X direction as shown in FIG. 1 with the imaging optical system 14 being interposed therebetween. The first displacement sensor 18a and the second displacement sensor 18b in this embodiment are laser displacement meters, which irradiate the culture container 50 with laser light and detect its reflection light to detect a position of a bottom surface of the culture container 50 in the Z direction. The bottom surface of the culture container 50 refers to a boundary surface with cells that correspond to an observation target, that is, a surface on which the observation target is placed.

Due to a difference between the culture container 50 and a refractive index of air, the position of the bottom surface of the culture container 50 in the Z direction detected by the first and second displacement sensors 18a and 18b is an apparent position, which is different from an actual position of the bottom surface of the culture container 50. In the present embodiment, the first and second displacement sensors 18a and 18b detect the position of the bottom surface of the culture container 50 in the Z direction and a position of a surface that is opposite to the bottom surface of the culture container 50 (that is, a surface of the culture container 50 on the stage side, which is hereinafter referred to as a lowest surface) in a Z direction. In the present embodiment, as will be described later, the apparent thickness of the bottom portion of the culture container 50 is derived using the positions of the bottom surface and the lowest surface of the culture container 50 detected by the detection section 18, and after the apparent thickness of the bottom portion of the culture container 50 is corrected on the basis of the difference between the culture container 50 and the refractive index of air, the actual position of the bottom surface of the culture container 50 in the Z direction is derived. Here, the bottom portion of the culture container 50 refers to a portion between the bottom surface and the lowest surface of the culture container 50.

The derivation of the actual position of the bottom surface of the culture container 50 in the Z direction will be described later. The detection section 18 outputs position information indicating the respective positions of the bottom surface and the lowest surface of the detected culture container 50.

The position information of the culture container 50 in the Z direction detected by the detection section 18 is output to an imaging optical system controller 21 which will be described later. The imaging optical system controller 21 adjusts an imaging position of the observation target on the basis of an adjustment value according to the input position information to perform the auto-focus control. In the present embodiment, the imaging optical system controller 21 controls the imaging position adjustment section 15 on the basis of the adjustment value to perform the auto-focus control. The auto-focus control based on the position of the culture container 50 in the Z direction detected by the detection section 18 will be described later.

Further, a stage 51 is provided between the slit plate 13, the phase difference lens 14a and the detection section 18. A culture container 50 in which cells that correspond to an observation target are contained is installed on the stage 51.

The culture container 50 corresponds to the transparent container of the present disclosure. As the culture container 50, a petri dish, a dish, a flask, a well plate, or the like may be used. Further, as the container, a slide glass, a microchannel device in which a fine channel is processed, or the like may be used. Although the culture container 50 is transparent, the culture container 50 is not limited to a container that transmits light of all wavelengths, but instead, may be a container that transmits only light of a specific wavelength. In this embodiment, a well plate having six wells W is used as the culture container 50.

In addition, as cells contained in the culture container 50, multipotential stem cells such as iPS cells and ES cells, cells of nerves, the skin, the myocardium and the liver differentiated and induced from a stem cell, cells of the skin, the retina, the myocardium, blood corpuscles, nerves, and organs extracted from a human body, and the like, may be used.

The stage 51 is configured to be moved in the X direction and a Y direction that are orthogonal to each other by a horizontal driving section 17 (see FIG. 4) which will be described later. The X direction and the Y direction are directions that are orthogonal to the Z direction, and are directions that are orthogonal to each other in a horizontal plane. In this embodiment, the X direction is referred to as a main scanning direction, and the Y direction is referred to as a sub-scanning direction.

FIG. 3 is a diagram showing an example of the stage 51. At the center of the stage 51, a rectangular opening 51a is formed. The culture container 50 is installed on a member that is formed with the opening 51a, and a phase difference image of cells in the culture container 50 passes through the opening 51a.

The imaging position adjustment section 15 is an actuator such as a piezoelectric element, and is driven by an imaging optical system controller 21 to be described later. In the present embodiment, the imaging position adjustment section 15 is a piezoelectric element, and the imaging optical system controller 21 controls an applied voltage to the imaging position adjustment section 15. The imaging position adjustment section 15 is configured to pass the phase difference image that has passed through the phase difference lens 14a and the imaging lens 14d as it is. Further, the imaging position adjustment section 15 is not limited to the piezoelectric element, and may use other known configurations as long as the objective lens 14b (phase difference lens 14a) can be moved in the Z direction.

The first displacement sensor 18a and the second displacement sensor 18b are supported by a support member 30a and a support member 30b, respectively. Further, the imaging optical system 14 is supported by a support member 31 through the imaging position adjustment section 15. Further, the support member 30a, the support member 30b, and the support member 31 are supported by a base 32 in the device. The support member 30a, the support member 30b, and the support member 31 are made of a metal material such as aluminum or brass.

First temperature sensors 41a and 41b that measure the respective temperatures of the support members 30a and 30b are attached to the support members 30a and 30b. A second temperature sensor 42 that measures the temperature of the support member 31 is attached to the support member 31. Further, a third temperature sensor 43 that measures the temperature of the culture container 50 is attached to the stage 51. The first temperature sensors 41a and 41b, the second temperature sensor 42, and the third temperature sensor 43 are made of a thermocouple or a non-contact sensor. The first temperature sensors 41a and 41b, the second temperature sensor 42, and the third temperature sensor 43 correspond to a first temperature measuring section, a second temperature measuring section, and a third temperature measuring section, respectively. The third temperature sensor 43 measures the temperatures of the plurality of wells W in the culture container 50, respectively. Thus, it is preferable that the third temperature sensor 43 is a non-contact sensor. Temperature information indicating a first temperature T1, a second temperature T2, and a third temperature T3 detected by the first temperature sensors 41a and 41b, the second temperature sensor 42, and the third temperature sensor 43 is output to the imaging optical system controller 21 to be described later.

Figure 4:
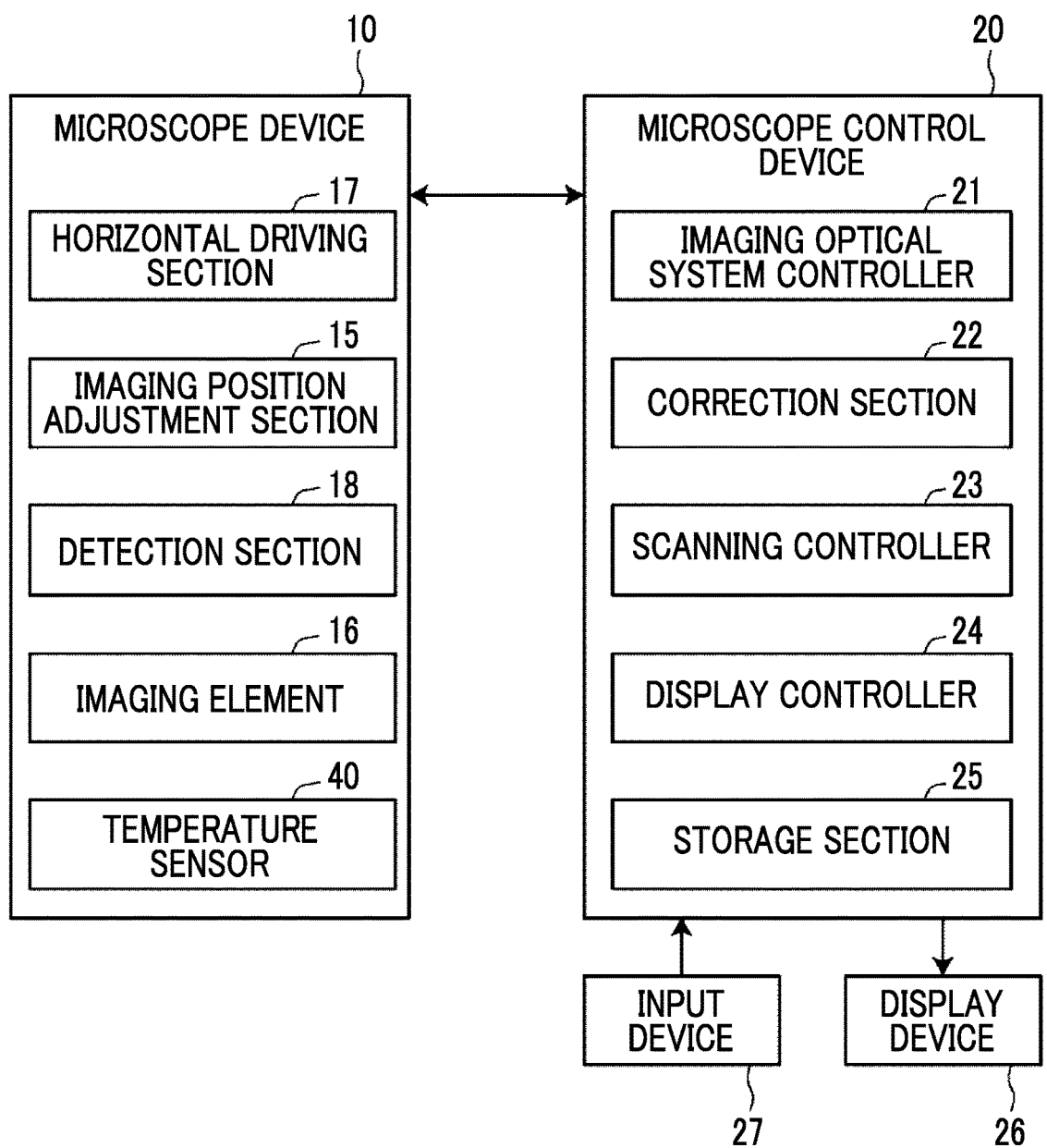
FIG. 4 is a block diagram showing a schematic configuration of a microscope observation system that uses an observation device according to a first embodiment of the present disclosure.

Then, a configuration of the microscope control device 20 that controls the microscope device 10 will be described. FIG. 4 is a block diagram showing a configuration of the microscope observation system according to this embodiment. With respect to the microscope device 10, a block diagram of a partial configuration controlled by respective sections of the microscope control device 20 is shown. Further, in the microscope device 10, the first temperature sensors 41a and 41b, the second temperature sensor 42, and the third temperature sensor 43 are represented by a temperature sensor 40.

The microscope control device 20 generally controls the microscope device 10, and particularly, includes an imaging optical system controller 21, a correction section 22, a scanning controller 23, a display controller 24, and a storage section 25.

The microscope control device 20 is configured of a computer provided with a central processing unit such as a CPU, a semiconductor memory, a hard disk, and the like, in which an observation device control program according to an embodiment of the present disclosure is installed in the hard disk.

Further, as the observation device control program is executed by the central processing unit, the imaging optical system controller 21, the correction section 22, and the scanning controller 23, and the display controller 24 shown in FIG. 4 perform their functions. Note that a semiconductor memory, a hard disk, and the like are shown as the storage section 25 in FIG. 4.

The imaging optical system controller 21 controls the imaging position adjustment section 15 on the basis of an adjustment value C0 according to the position information indicating the position of the culture container 50 in the Z direction detected by the detection section 18 as described above. In the present embodiment, the adjustment value C0 is an applied voltage to the imaging position adjustment section 15 (that is, the piezoelectric element). The piezoelectric element expands and contracts according to the applied voltage. Accordingly, the objective lens 14b of the imaging optical system 14 is moved in the optical axis direction by driving the imaging position adjustment section 15 according to the applied voltage from the imaging optical system controller 21, so that the auto-focus control is performed.

Figure 5:
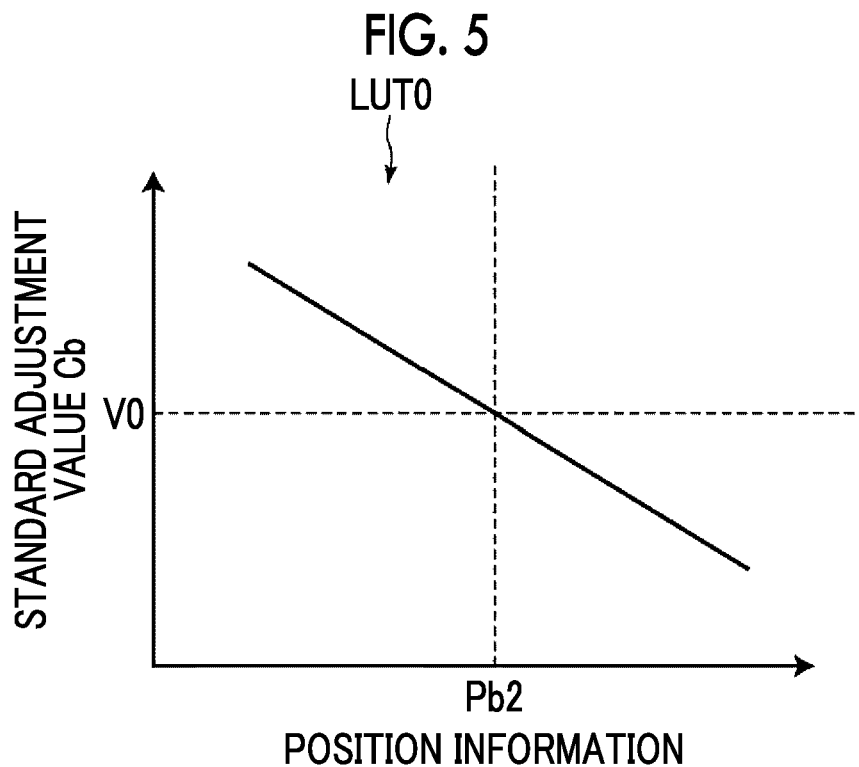
FIG. 5 is a diagram showing a relationship between position information and an adjustment value.

In the present embodiment, the storage section 25 stores a relationship between the position information of the bottom surface of the culture container 50 and the adjustment value (that is, the applied voltage to the piezoelectric element) as a lookup table LUT0 as shown in FIG. 5. The lookup table LUT0 represents a relationship between position information at a predetermined standard temperature Tb and a standard adjustment value (hereinafter referred to as a standard adjustment value) Cb.

In the present embodiment, the objective lens 14b is attached to the microscope device 10 so as to focus on the bottom surface of the culture container 50 at the standard position in the case of the standard temperature Tb. This attachment position is set to a standard position Pb1 of the objective lens 14b. Further, the position of the bottom surface of the culture container 50, which is the standard in this case, is set to a standard position Pb2. In a case where the objective lens 14b is positioned at the standard position Pb1 and the bottom surface of the culture container 50 is positioned at the standard position Pb2, the position of the bottom surface of the culture container 50 is the focusing position of the objective lens 14b. Accordingly, in a case where the support members 30a and 30b and the support member 31 are at the standard temperature Tb and in a case where the position of the bottom surface of the culture container 50 detected by the detection section 18 is the standard position Pb2 as described later, the applied voltage to the imaging position adjustment section 15 is a standard applied voltage (hereinafter, referred to as a standard voltage) V0 in the lookup table LUT0 shown in FIG. 5 in order to move the position of the objective lens 14b to the standard position Pb1.

The imaging optical system controller 21 derives a standard adjustment value Cb from the position information detected by the detection section 18 with reference to the lookup table LUT0. In a case where the temperatures of the support members 30a and 30b, and the support member 31 are at the standard temperature Tb, the imaging position adjustment section 15 is controlled on the basis of the standard adjustment value Cb, and thus, the objective lens 14b is moved in the Z direction so that the position of the bottom surface of the culture container 50 becomes the focusing position of the illumination light L0. Accordingly, the image of the observation target is formed by the imaging element 16, and thus, it is possible to appropriately perform the auto-focus control. In the present embodiment, a coordinate system of the detection section 18 is set so that as the position information detected by the detection section 18 becomes larger, the distance between the detection section 18 and the culture container 50 becomes smaller. Accordingly, in the lookup table LUT0 shown in FIG. 5, as the position information becomes larger, the value of the standard adjustment value Cb becomes smaller. Thus, as the position information becomes larger, that is, as the distance between the detection section 18 and the culture container 50 becomes smaller, the objective lens 14b is more distant from the culture container 50.

The correction section 22 corrects the standard adjustment value Cb. Hereinafter, the correction of the standard adjustment value Cb will be described. The correction section 22 receives first temperature information representing the first temperature T1 that correspond to the temperatures of the support members 30a and 30b measured by the first temperature sensors 41a and 41b, second temperature information representing the second temperature T2 that is the temperature of the support member 31 measured by the second temperature sensor 42, and third temperature information representing the third temperature T3 that is the temperature of the culture container 50 measured by the third temperature sensor 43, as inputs. The support members 30a and 30b are made of metal, and expand and contract according to change in temperature. Accordingly, in a case where the temperatures of the support members 30a and 30b are changed, the positions of the displacement sensors 18a and 18b in the Z direction are changed. Further, the support member 31 is also made of metal, and expands and contracts according to change in temperature. Accordingly, in a case where the temperature of the support member 31 is changed, the position of the objective lens 14b in the Z direction is changed.

As described above, the standard adjustment value Cb is derived according to the position information indicating the position of the bottom surface of the culture container 50 detected by the displacement sensors 18a and 18b at the standard temperature Tb. Here, in a case where the first temperature T1 is not the standard temperature Tb, the positions of the tips of the displacement sensors 18a and 18b in the Z direction are different from the positions thereof at the standard temperature Tb. In a case where the second temperature T2 is not the standard temperature Tb, the position of the objective lens 14b in the Z direction is different from the position thereof at the standard temperature Tb. Accordingly, even in a case where the position of the objective lens 14b in the Z direction is controlled on the basis of the standard adjustment value Cb, the position of the bottom surface of the culture container 50 is different from the focusing position of the objective lens 14b, and thus, it is not possible to appropriately perform the auto-focus control.

Figure 6:
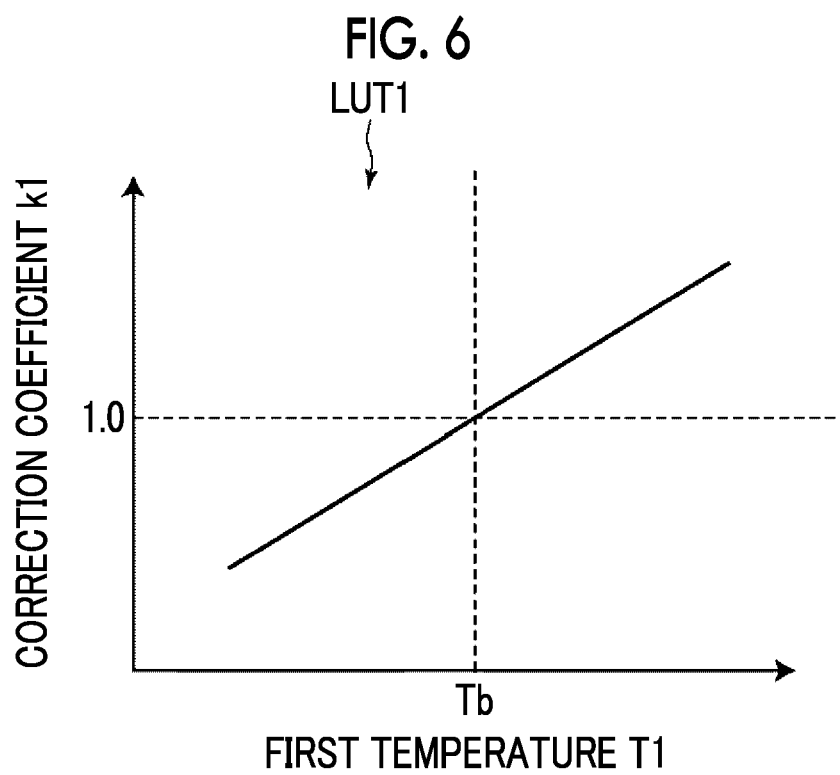
FIG. 6 is a diagram showing a relationship between a first temperature and a correction coefficient.
Figure 7:
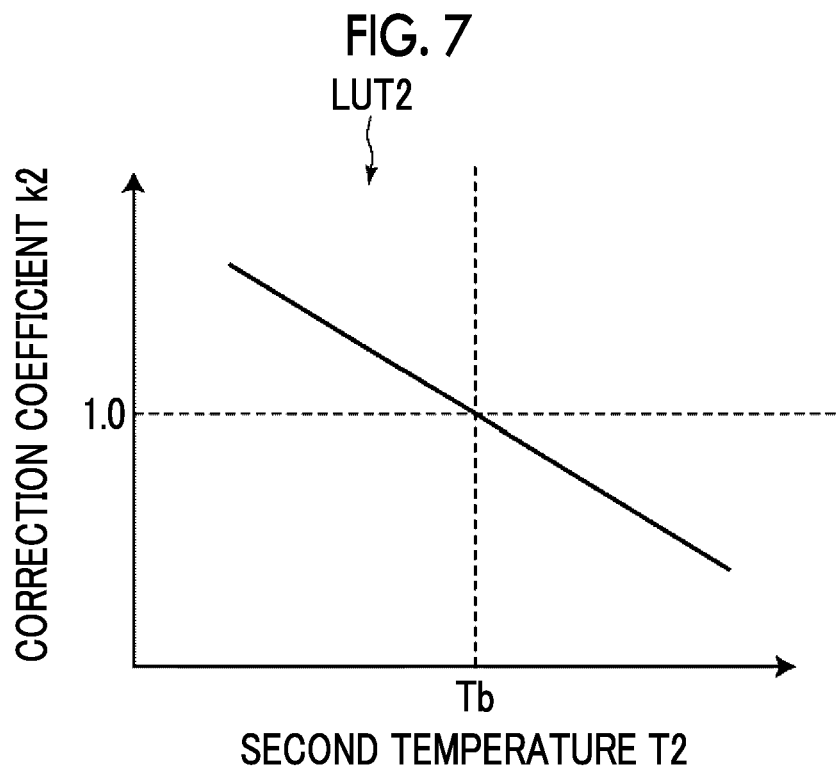
FIG. 7 is a diagram showing a relationship between a second temperature and a correction coefficient.

Accordingly, the correction section 22 corrects the standard adjustment value Cb. Specifically, the correction section 22 first derives correction coefficients k1 and k2 for correcting the standard adjustment value Cb on the basis of the first temperature T1 and the second temperature T2. In the present embodiment, the storage section 25 stores a lookup table LUT1 that defines a relationship between the first temperature T1 and the correction coefficient k1 for the standard adjustment value Cb, and a lookup table LUT2 that defines a relationship between the second temperature T2 and the correction coefficient k2 for the standard adjustment value Cb. FIGS. 6 and 7 are diagrams showing the lookup tables LUT1 and LUT2, respectively. The lookup table LUT1 represents the relationship between the first temperature T1 and the correction coefficient k1 in a case where the correction coefficient k1 at the standard temperature Tb is set to 1.0. Here, since in a case where the first temperature T1 is high, the support members 30a and 30b are expanded, the distance between the detection section 18 and the culture container 50 becomes small. Thus, the position information detected by the detection section 18 becomes large, so that the standard adjustment value Cb becomes small as shown in FIG. 5. In this case, it is necessary to increase the standard adjustment value Cb so that the distance between the objective lens 14b and the culture container 50 becomes small. Accordingly, as shown in FIG. 6, in the lookup table LUT1, as the first temperature T1 becomes higher, the value of the correction coefficient k1 becomes larger.

The lookup table LUT2 represents the relationship between the second temperature T2 and the correction coefficient k2 in a case where the correction coefficient k2 at the standard temperature Tb is set to 1.0. Here, since in a case where the second temperature T2 is high, the support member 31 extends, the distance between the objective lens 14b and the culture container 50 becomes small. In this case, it is necessary to reduce the standard adjustment value Cb so that the distance between the objective lens 14b and the culture container 50 becomes large. Accordingly, as shown in FIG. 7, in the lookup table LUT2, as the second temperature T2 becomes higher, the value of the correction coefficient k2 becomes smaller. The lookup table LUT1 corresponds to a first lookup table, the correction coefficient k1 corresponds to a first correction coefficient, the lookup table LUT2 corresponds to a second lookup table, and the correction coefficient k2 corresponds to a second correction coefficient.

The correction section 22 derives the correction coefficient k1 on the basis of the first temperature T1 with reference to the lookup table LUT1. Further, the correction section 22 derives the correction coefficient k2 on the basis of the second temperature T2 with reference to the lookup table LUT2. Accordingly, by adjusting the position of the objective lens 14b in the Z direction by an adjustment value derived by multiplying the standard adjustment value Cb by the correction coefficient k1 and the correction coefficient k2, the focal position of the objective lens 14b is located on the bottom surface of the culture container 50 regardless of the temperatures of the support members 30a and 30b, and the support member 31.

Figure 8:
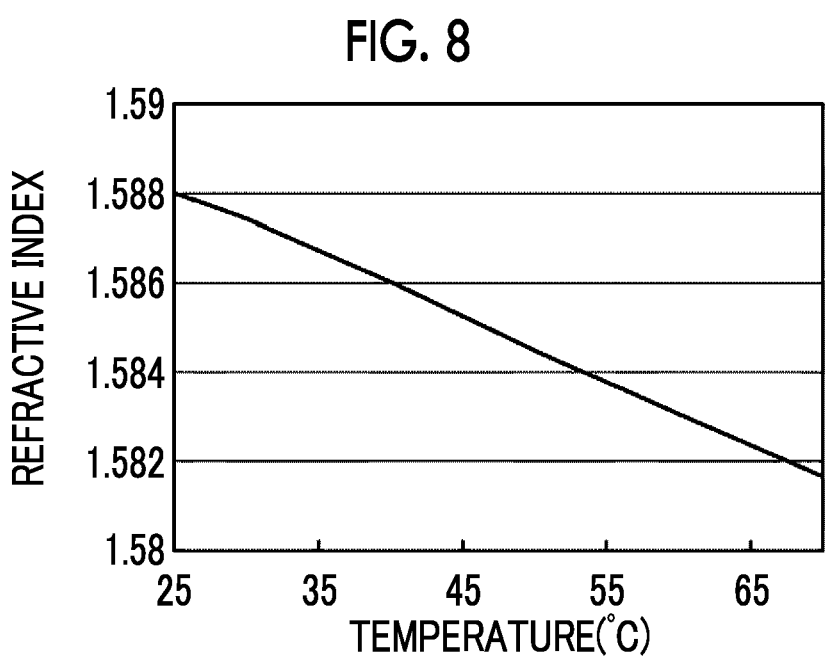
FIG. 8 is a diagram showing a relationship between a temperature and a refractive index of a material that forms a well plate.

In the present embodiment, the correction section 22 further derives a correction coefficient k3 for correcting the standard adjustment value Cb on the basis of the third temperature T3 represented by the third temperature information. In the present embodiment, the culture container 50 is made of a resin material such as polystyrene. A refractive index of the resin material changes depending on temperature. FIG. 8 is a diagram showing a relationship between a temperature and a refractive index in polystyrene. As shown in FIG. 8, in the polystyrene, as the temperature becomes higher, the refractive index becomes smaller.

Figure 9:
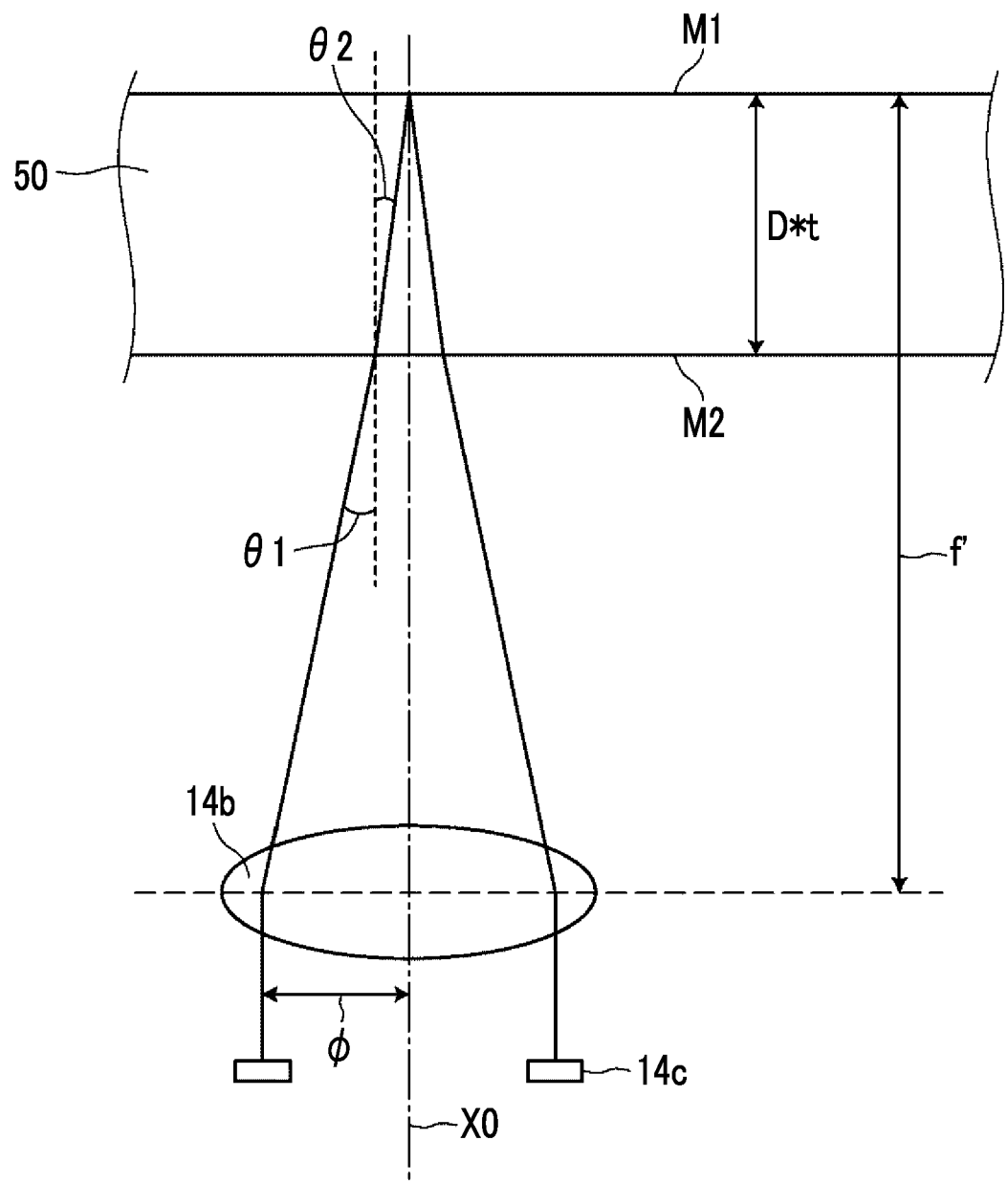
FIG. 9 is a diagram showing an optical path of an objective lens in a state of being in focus on a bottom surface of a culture container.

FIG. 9 is a diagram showing an optical path of the objective lens 14b in a state of being in focus on the bottom surface of the culture container 50. In FIG. 9, M1 represents the bottom surface of the culture container 50, M2 represents a lowest surface of the culture container 50, X0 represents an optical axis of an illumination light L0, θ1 represents an emission angle of the illumination light L0 emitted from the culture container 50, θ2 represents an incidence angle of the illumination light L0 from the culture container 50 to air, D represents an apparent thickness of the bottom portion of the culture container 50 derived from the position information detected by the detection section 18, t represents a thickness correction coefficient in consideration of the refractive index of the material of the culture container 50, f represents a focal length of the objective lens 14b in a case where the culture container 50 is present, and φ represents the radius of the phase plate 14c.

Figure 10:
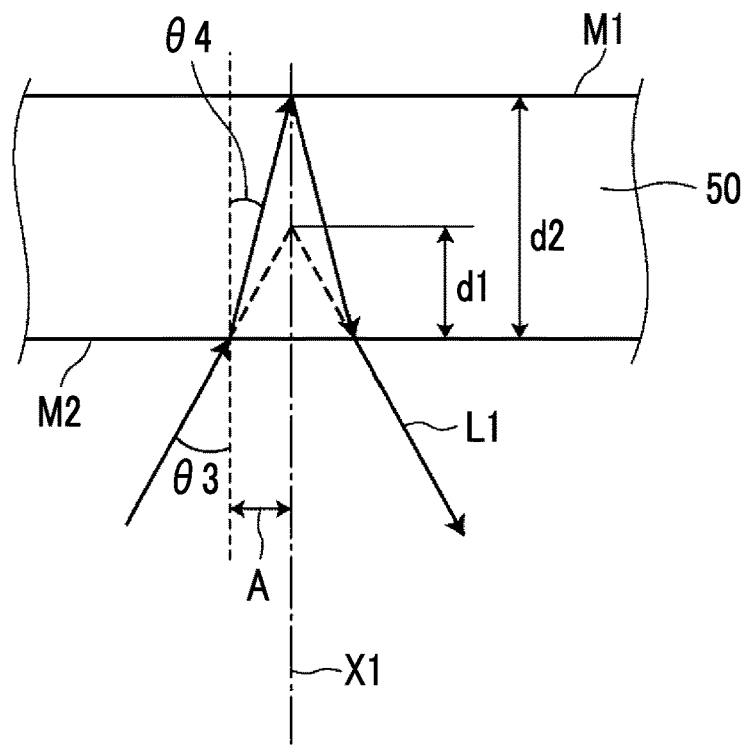
FIG. 10 is a diagram for illustrating derivation of a thickness correction coefficient.

First, the thickness correction coefficient t will be described. The thickness correction coefficient t is a coefficient for correcting an apparent thickness of the bottom portion of the culture container 50 to an actual thickness. FIG. 10 is a diagram for illustrating derivation of the thickness correction coefficient. Here, in a case where the thickness of a material having a refractive index larger than that of air is measured, the apparent thickness shifts toward thinner. In FIG. 10, θ3 represents an incidence angle of the laser light L1 emitted from the displacement sensors 18a and 18b incident on the culture container 50, θ4 represents an emission angle of a laser light L1 from air, d1 represents an apparent thickness of the bottom portion of the culture container 50 detected by the displacement sensors 18a and 18b, d2 represents an actual thickness of the bottom portion of the culture container 50, X1 represents a normal line of the laser light L1 at a boundary between the culture container 50 and air at the bottom surface M1 of the culture container 50, A represents a distance between the normal line X1 on an incidence surface of the laser light L1 and an incidence position of the laser light L1. The incidence angle θ3 of the laser light L1 depends on the displacement sensors 18a and 18b. Further, the thickness d1 may be derived by subtracting the distance to the lowest surface M2 from the distance to the bottom surface M1 of the culture container 50 detected by the displacement sensors 18a and 18b.

Here, assuming that the refractive index of air is n1 and the refractive index of the material of the culture container 50 is n2, θ4=sin$^{-1}$(n1·sin θ3/n2) according to the Snell's law. Further, since tan θ3=A/d1 and tan θ4=A/d2, tan θ4=d1·tan θ1/d2. Further, since the thickness correction coefficient t is the coefficient for correcting the apparent thickness of the bottom portion of the culture container 50 to the actual thickness, d1·t=d2. Accordingly, the thickness correction coefficient t is calculated by the following equation (1).

$$t = \tan\theta_3/\tan\theta_4 = \tan\theta_3/\tan[\sin^{-1}(n_1 \cdot \sin\theta_3/n_2)] \qquad (1)$$

Accordingly, in a case where the incidence angle θ3 of the laser light L1 emitted from the displacement sensors 18a and 18b and the refractive index n2 of the material of the culture container 50 are known, the thickness correction coefficient t may be calculated by the above equation (1). Thus, by deriving the apparent thickness of the bottom portion of the culture container 50 from the position information detected by the displacement sensors 18a and 18b and multiplying the derived apparent thickness of the bottom portion of the culture container 50 by the thickness correction coefficient t, it is possible to derive the actual thickness of the bottom portion of the culture container 50. As shown in FIG. 8, since the refractive index n2 of the material changes according to the temperature, the correction coefficient t changes according to the third temperature T3 that is the temperature of the culture container 50.

Returning to FIG. 9, assuming that the refractive index of air is n1 and the refractive index of the material of the culture container 50 is n2, the focal length f' of the objective lens 14b in a case where the culture container 50 is present is expressed by the following equation (2), similar to the description of the above equation (1). In the equation (2), f is the focal length of the objective lens 14b in a case where the culture container 50 is not present.

[Expression 1]

$$f' = D*t + \frac{f\left(\phi - D*t*\tan\left(\sin^{-1}\left(\frac{n_1}{n_2}\sin\theta_1\right)\right)\right)}{\phi} \qquad (2)$$

$$= f + D*t*\left(1 - \frac{f*\tan\left(\sin^{-1}\left(\frac{n_1}{n_2}\sin\theta_1\right)\right)}{\phi}\right)$$

Figure 11:
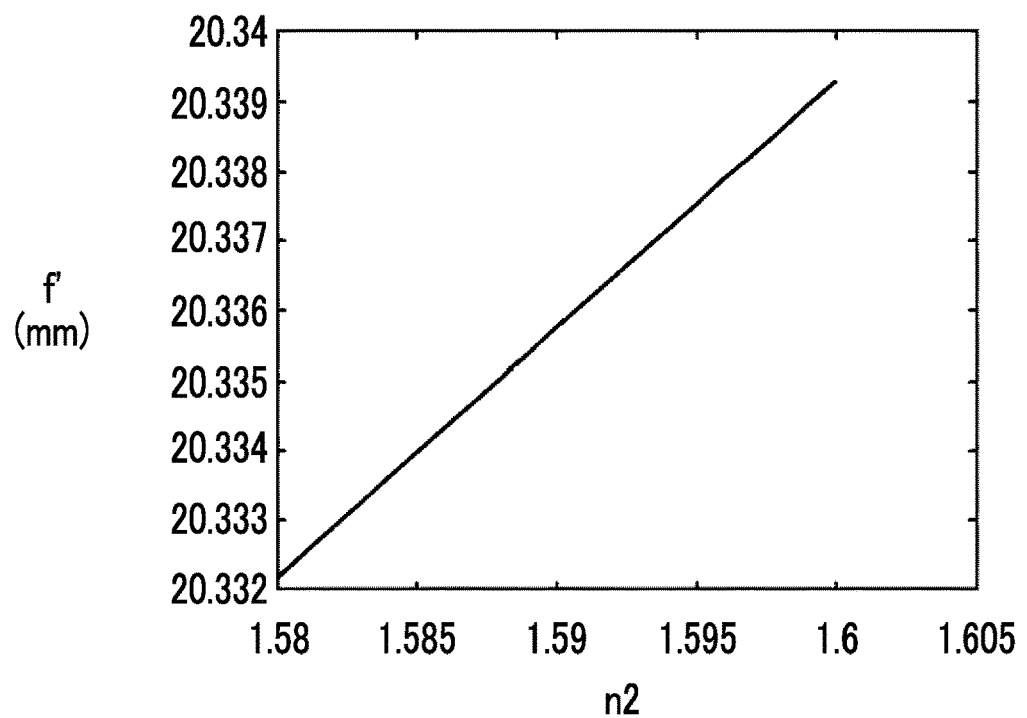
FIG. 11 is a diagram showing a relationship between a material that forms a well plate and a focal length of an objective lens.

On the basis of the relationships shown in the equations (1) and (2), the relationship between the refractive index n2 of the culture container 50 and the focal length f of the objective lens 14b may be calculated. FIG. 11 is a diagram showing an example of the relationship between the refractive index of the culture container 50 and the focal length f of the objective lens 14b. As shown in FIG. 11, as the refractive index n2 becomes larger, the focal length of the objective lens 14b becomes larger. Accordingly, the thickness correction coefficient t according to the third temperature T3 may be derived on the basis of the relationship between the temperature and the refractive index shown in FIG. 8 and the equation (1). Further, the focal length f of the objective lens 14b according to the third temperature T3 may be derived, using the derived thickness correction coefficient t, on the basis of the relationship between the refractive index and the focal length shown in FIG. 11 and the equation (2). Further, it is possible to derive an applied voltage to the imaging position adjustment section 15 for moving the objective lens 14b in the Z direction so that the derived focal length f is aligned with the bottom surface of the culture container 50. Further, a correction coefficient for the standard voltage V0 may be derived by dividing the derived applied voltage by the standard voltage V0.

Figure 12:
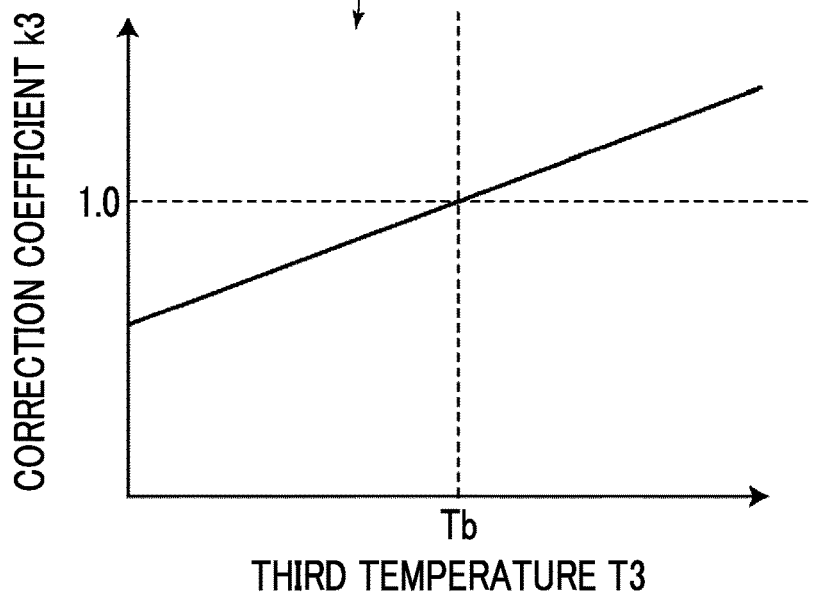
FIG. 12 is a diagram showing a relationship between a third temperature and a correction coefficient.

Accordingly, by deriving the applied voltage to the imaging position adjustment section 15 for various temperatures and dividing the result by the standard voltage V0, it is possible to obtain the relationship of the correction coefficient k3 of the standard adjustment value Cb with respect to the temperature of the culture container 50, that is, the third temperature T3. In the present embodiment, a lookup table that defines the relationship between the third temperature T3 and the correction coefficient k3 is generated in advance, and is stored in the storage section 25. FIG. 12 is a diagram showing the lookup table that defines the relationship between the third temperature T3 and the correction coefficient k3. A lookup table LUT3 represents the relationship between the third temperature T3 and the correction coefficient k3 in a case where the correction coefficient k3 at the standard temperature Tb is set to 1.0. Here, in a case where the third temperature T3 is high, the refractive index of the culture container 50 decreases as shown in FIG. 8, and as a result, the focal length of the objective lens 14b decreases as shown in FIG. 11. In this case, it is necessary to increase the standard adjustment value Cb so that the distance between the objective lens 14b and the culture container 50 becomes small. Accordingly, as shown in FIG. 12, in the lookup table LUT3, as the third temperature T3 becomes higher, the value of the correction coefficient k3 becomes larger. The lookup table LUT3 corresponds to a third lookup table, and the correction coefficient k3 corresponds to a third correction coefficient.

The correction section 22 derives the correction coefficients k1 to k3 from the first to third temperatures with reference to the above-mentioned lookup tables LUT1 to LUT3. Then, the correction section 22 corrects the standard adjustment value Cb by the following equation (3) to calculate a corrected adjustment value C0.

$$C0 = Cb \cdot k1 \cdot k2 \cdot k3 \quad (3)$$

In the above embodiment, the lookup tables LUT1 to LUT3 are stored in the storage section 25, the correction coefficients k1 to k3 are derived with reference to the lookup tables LUT1 to LUT3 to correct the standard adjustment value Cb, and the adjustment value C0 is derived, but the present disclosure is not limited thereto. An arithmetic expression for correcting the standard adjustment value Cb according to the first to third temperatures T1 to T3 may be stored in the storage section 25, and the adjustment value C0 may be derived according to the first to third temperatures T1 to T3.

The scanning controller 23 controls driving of the horizontal driving section 17, to thereby move the stage 51 in the X direction and the Y direction, and move the culture container 50 in the X direction and the Y direction. The horizontal driving section 17 is configured by an actuator such as a piezoelectric element.

Hereinafter, the movement control of the stage 51 by the scanning controller 23 and the auto-focus control by the imaging optical system controller 21 will be described in detail.

Figure 13:
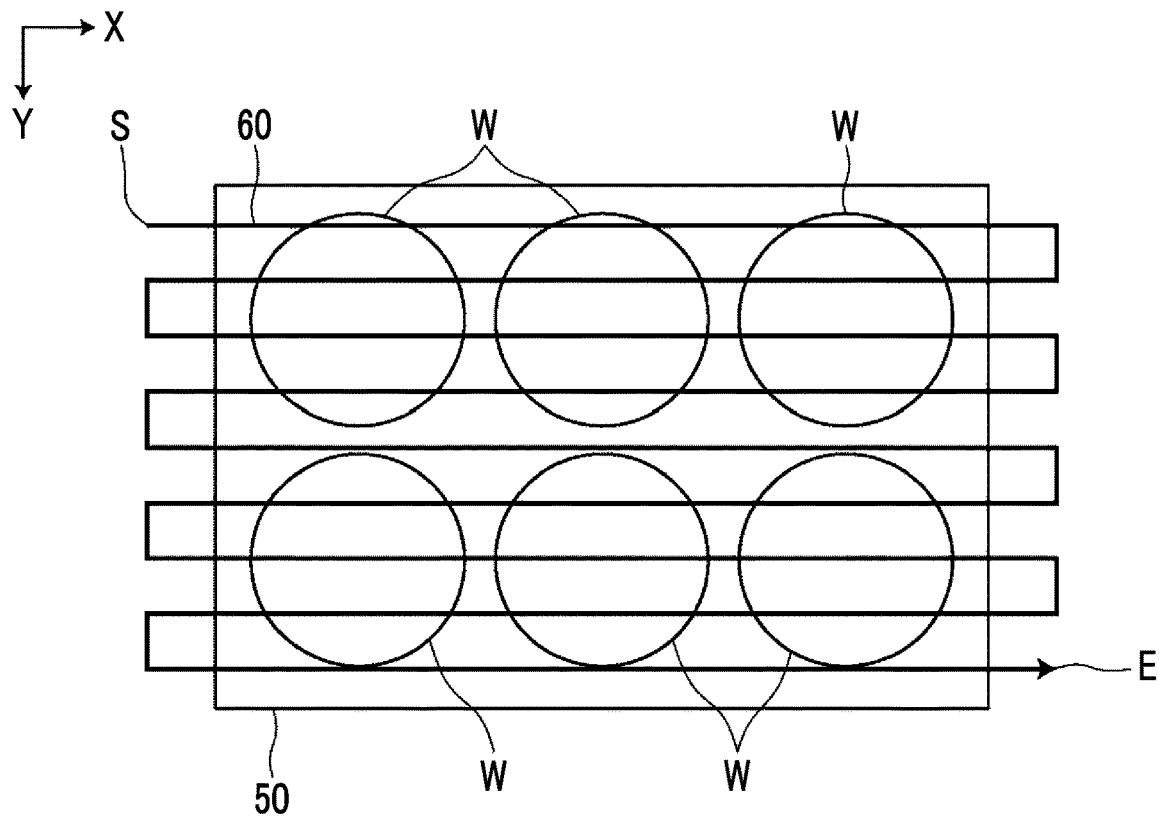
FIG. 13 is a diagram showing a scanning position of an observation region in a culture container.

In this embodiment, the stage 51 is moved in the X direction and the Y direction under the control of the scanning controller 23, so that the observation region of the imaging optical system 14 is moved in a two-dimensional manner in the culture container 50 to scan the culture container 50, and a phase difference image at each observation region in the culture container 50 is captured. FIG. 13 is a diagram showing a scanning position based on an observation region in the culture container 50 using a solid line 60. In this embodiment, the culture container 50 has 6 wells W.

As shown in FIG. 13, the observation region of the imaging optical system 14 is moved along the solid line 60 from a scanning start point S to a scanning end point E. That is, the observation region is moved in a positive direction (a rightward direction in FIG. 6) of the X direction, is moved in the Y direction (a downward direction in FIG. 13), and then, is moved in a reverse negative direction (in a leftward direction in FIG. 6). The observation region is then moved again in the Y direction and again in the positive direction. In this way, by repeating the reciprocating movement of the observation region in the X direction and the movement thereof in the Y direction, the culture container 50 is scanned in a two-dimensional manner.

Figure 14:
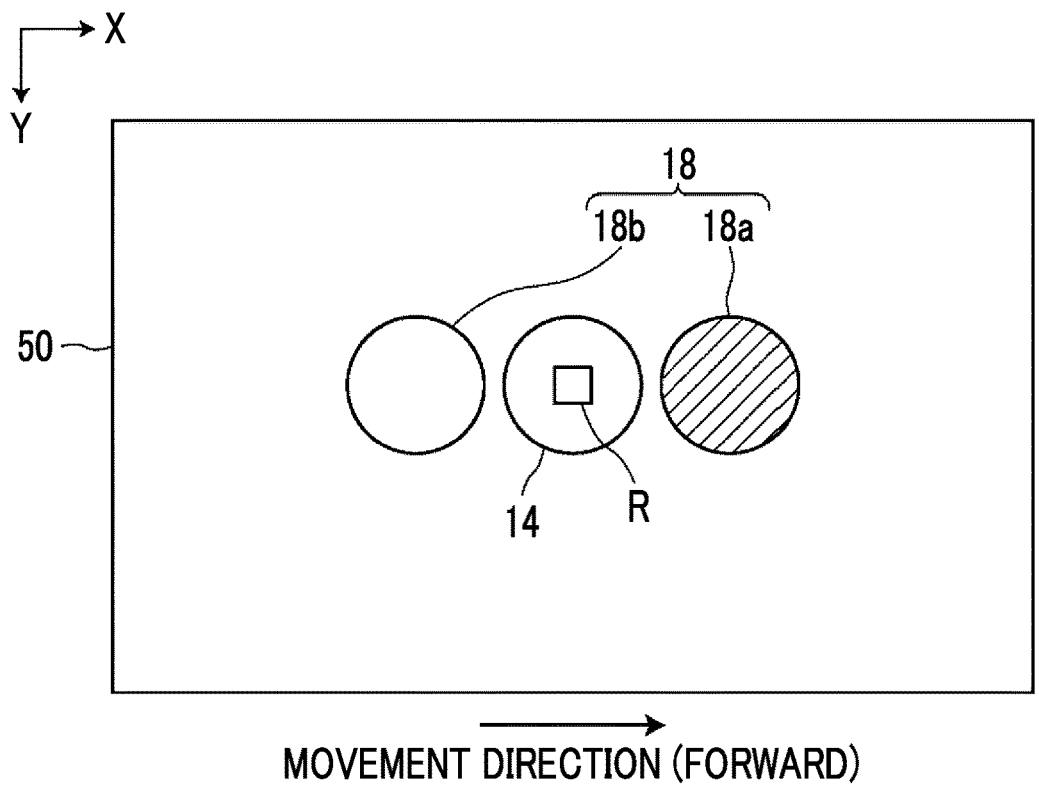
FIG. 14 is a diagram showing a positional relationship between an imaging optical system, a first displacement sensor, a second displacement sensor, and a culture container in a case where there is an observation region at an arbitrary position in the culture container.
Figure 15:
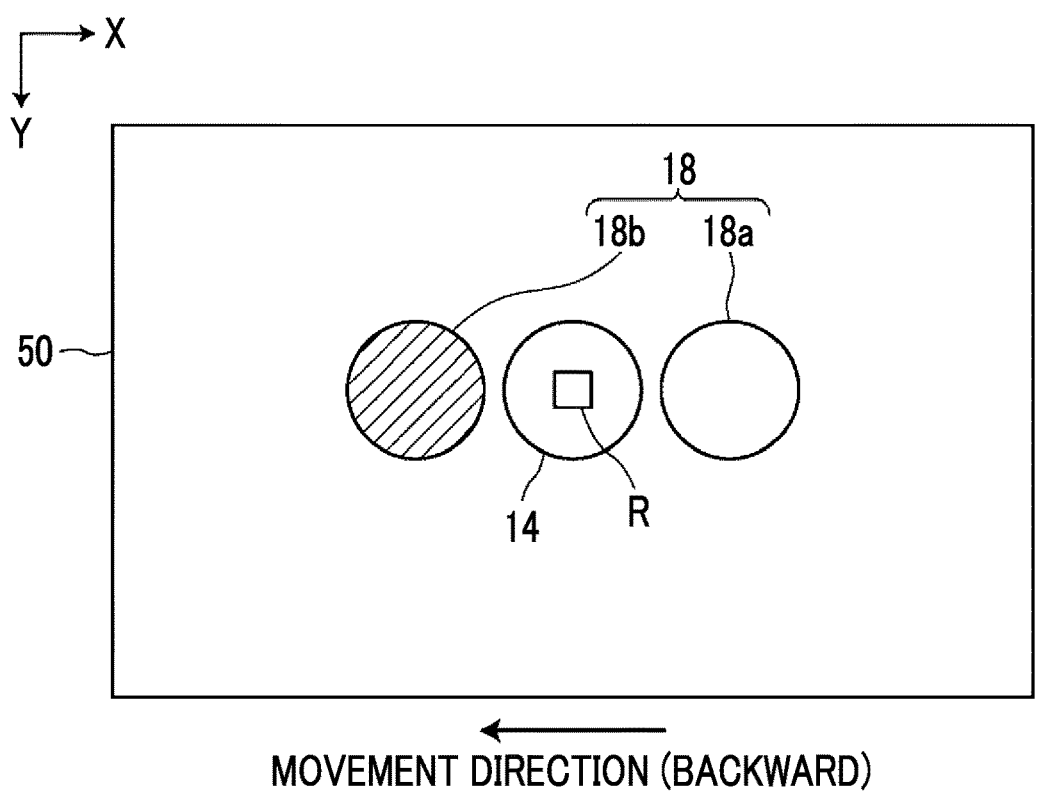
FIG. 15 is a diagram for illustrating switching between the first displacement sensor and the second displacement sensor.

FIGS. 14 and 15 are diagrams showing positional relationships between the imaging optical system 14, the first displacement sensor 18a, the second displacement sensor 18b, and the culture container 50 in a case where an observation region R is present at an arbitrary position in the culture container 50.

In the present embodiment, as shown in FIGS. 14 and 15, the first displacement sensor 18a and the second displacement sensor 18b are provided side by side in the X direction with the imaging optical system 14 being interposed therebetween. Then, the observation region R of the imaging optical system 14 is moved in a two-dimensional manner in the culture container 50 as described above, and in this case, the position of the culture container 50 in the Z direction is detected at a position in front of a position of the observation region R of the imaging optical system 14 with respect to the culture container 50 in a movement direction of the observation region R. Specifically, in a case where the observation region R is moving in an arrow direction shown in FIG. 14 (a rightward direction in FIG. 14), the position of the culture container 50 in the Z direction (in this case, including the position of the bottom surface and the lowest surface of the culture container 50 in the Z direction) is detected by the first displacement sensor 18a in front of the observation region R in the movement direction, among the first displacement sensor 18a and the second displacement sensor 18b. Then, in a case where the observation region R is moved from the position shown in FIG. 14 to the position where the position of the culture container 50 in the Z direction is detected by the first displacement sensor 18a, the auto-focus control is performed using information on the position of the culture container 50 in the Z direction detected in advance, and then, a phase difference image is captured.

On the other hand, in a case where the observation region R is moving in an arrow direction in FIG. 15 (a leftward direction in FIG. 15), the position of the culture container 50 in the Z direction is detected by the second displacement sensor 18b in front of the observation region R in the movement direction, among the first displacement sensor 18a and the second displacement sensor 18b. Then, in a case where the observation region R is moved from the position shown in FIG. 15 to the position where the position of the culture container 50 in the Z direction is detected by the second displacement sensor 18b, the auto-focus control is performed using information on the position of the culture container 50 in the Z direction detected in advance, and then, a phase difference image is captured.

By performing switching between the detection of the culture container 50 using the first displacement sensor 18a and the detection of the culture container 50 using the second displacement sensor 18b according to the movement direction of the observation region R, it is possible to constantly acquire the information on the position of the culture container 50 in the Z direction at the position of the observation region R, prior to imaging the phase difference image of the observation region R.

Then, the imaging optical system controller 21 controls driving of the imaging position adjustment section 15 on the basis of the information on the position of the culture container 50 in the Z direction detected in advance as described above, to thereby perform the auto-focus control. Specifically, the imaging optical system controller 21 outputs the adjustment value C0 derived by the correction section 22 to the imaging position adjustment section 15, as described above. The imaging position adjustment section 15 is driven according to the input adjustment value C0, and thus, the objective lens 14b is moved in the Z direction, and auto-focus adjustment is performed according to the position of the bottom surface of the culture container 50 in the Z direction.

Next, returning to FIG. 4, the display controller 24 combines phase difference images at the respective observation regions R imaged by the microscope device 10 to generate one composite phase difference image, and displays the composite phase difference image on the display device 26.

The display device 26 displays the composite phase difference image generated by the display controller 24 as described above, and for example, includes a liquid crystal display, or the like. Further, the display device 26 may be formed by a touch panel, and may also be used as an input device 27.

The input device 27 includes a mouse, a keyboard, and the like, and receives various setting inputs by users.

Figure 16:
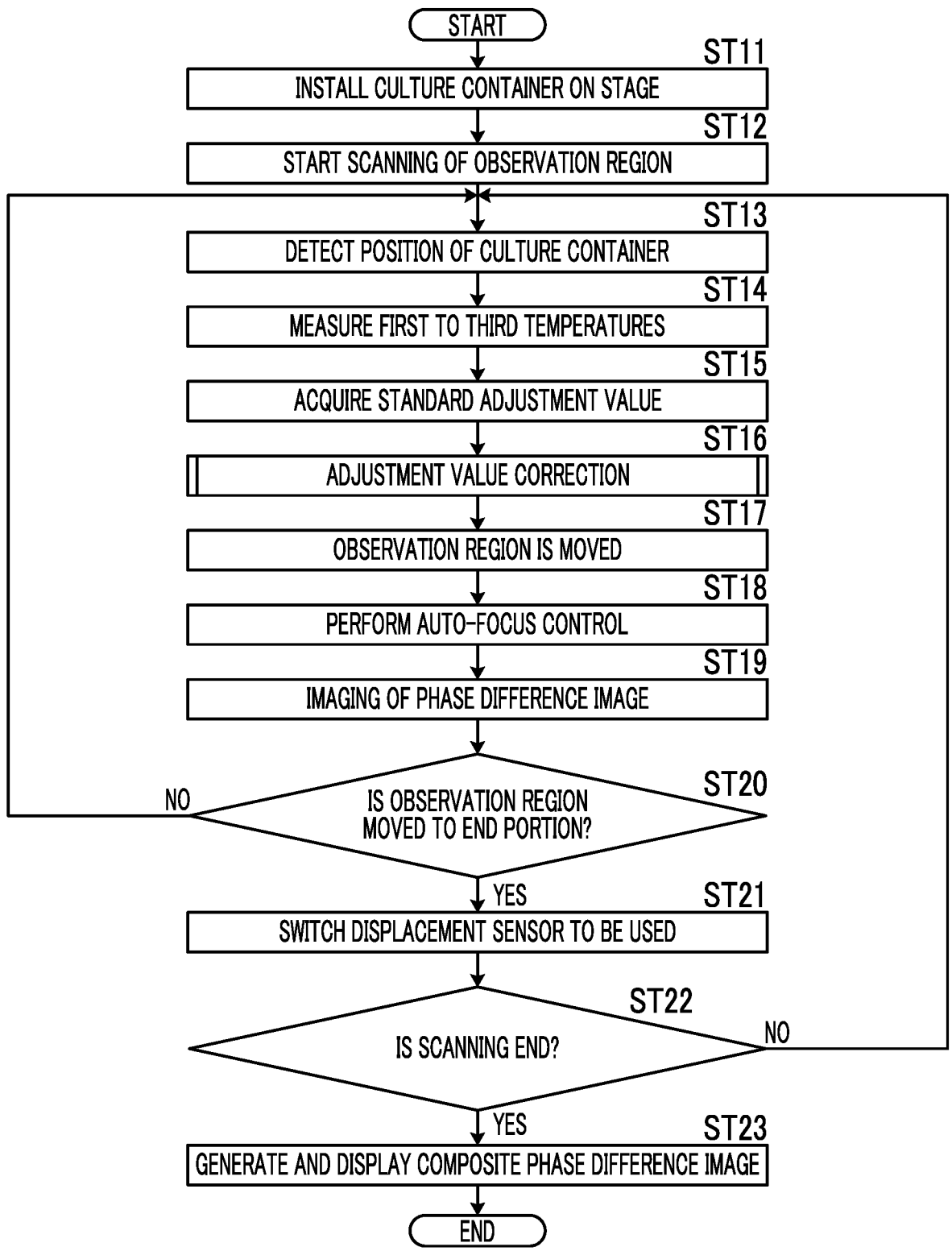
FIG. 16 is a flowchart for illustrating an operation of the microscope observation system that uses the observation device according to the first embodiment of the present disclosure.

Next, an operation of the microscope observation system according to this embodiment will be described with reference to a flowchart shown in FIG. 16. First, the culture container 50 in which cells that are observation targets are contained is installed on the stage 51 (step ST11). Then, the stage 51 is moved so that the observation region R of the imaging optical system 14 is set to the position of the scanning start point S shown in FIG. 13, and scanning based on the observation region R is started (step ST12).

Here, in this embodiment, as described above, the position of the culture container 50 is precedently detected with respect to each observation region R, and at a time point when the observation region R reaches the detection position, a phase difference image is captured. Further, the detection of the position of the culture container 50 and the capturing of the phase difference image are performed while moving the observation region R, and capturing of a phase difference image of the observation region R at a certain position and detection of the position of the culture container 50 at the position in front of the certain position in the movement direction are performed in parallel.

Specifically, in a case where the observation region R is moving in the arrow direction in FIG. 13, the position of the culture container 50 in the Z direction is detected by the first displacement sensor 18a (step ST13), the first to third temperatures T1 to T3 are measured by the first temperature sensors 41a and 41b, the second temperature sensor 42, and the third temperature sensor 43 (step ST14), the detected position information is acquired by the imaging optical system controller 21, and the measured temperature information is acquired by the correction section 22.

Figure 17:
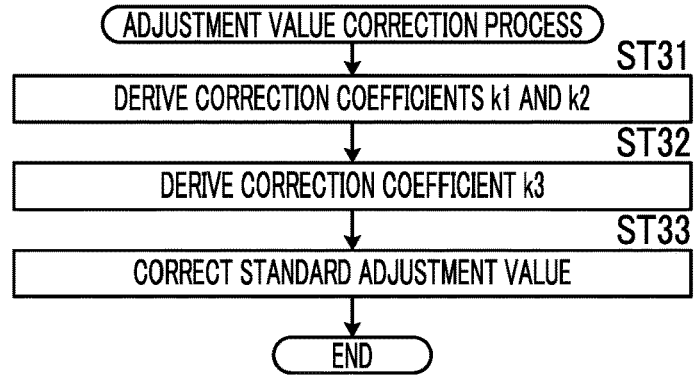
FIG. 17 is a flowchart for illustrating an adjustment value correction process.

The imaging optical system controller 21 acquires the standard adjustment value Cb with reference to the lookup table LUT0 on the basis of the detected position information (step ST15). Then, the correction section 22 derives the correction coefficients k1 to k3 on the basis of the temperature information, and corrects the standard adjustment value Cb (step ST16). FIG. 17 is a flowchart of an adjustment value correction process. The correction section 22 first derives the correction coefficients k1 and k2 on the basis of the first temperature T1 and the second temperature T2 (step ST31). Further, the correction section 22 derives the correction coefficient k3 on the basis of the third temperature T3 (step ST32). Then, the correction section 22 corrects the standard adjustment value Cb on the basis of the correction coefficients k1 to k3 (step ST33). Thus, the corrected adjustment value C0 is acquired, and then, the adjustment value correction process ends. The adjustment value C0 is stored in the storage section 25 in association with a position on the XY coordinates of the detection position of the culture container 50.

Returning to FIG. 16, the observation region R is moved toward the position where the position of the culture container 50 is detected by the first displacement sensor 18a in step ST17 (step ST17). Then, the imaging optical system controller 21 acquires the corrected adjustment value C0 just before the observation region R reaches the position where the position of the culture container 50 is detected, and performs the auto-focus control (step ST18). That is, the imaging optical system controller 21 controls the driving of the imaging position adjustment section 15 on the basis of the adjustment value C0 to move the objective lens 14b in the Z direction. Further, after the auto-focus control, at a time point when the observation region R reaches the position where the position of the culture container 50 is detected, imaging for a phase difference image is performed (step ST19). The phase difference image at each observation region R is output from the imaging element 16 to the display controller 24, and is stored. As described above, while the imaging for the phase difference image at the observation region R is being performed in step ST19, the position of the culture container 50 is detected in parallel at a forward position in the movement direction with reference to the observation region R.

Then, in a case where the observation region R is moved to an end portion of the culture container 50 (step ST20; YES), the observation region R is moved in the Y direction, and then, is moved in a reverse direction. That is, the movement direction changes from the arrow direction of FIG. 14 to the arrow direction in FIG. 15. The displacement sensor to be used is switched from the first displacement sensor 18a to the second displacement sensor 18b (step ST21). In a case where the observation region R is not moved to the end portion of the culture container (step ST20; NO), the position detection of the culture container 50 and the capturing of the phase difference image are sequentially performed (step ST13 to step ST19).

Then, in a case where the whole scanning is not completed (step ST22; NO), the observation region R is moved in the X direction again, and the position detection of the culture container 50 and the capturing of the phase difference image described above are sequentially performed (step ST13 to step ST19).

The displacement sensor to be used is switched whenever the observation region R is moved to the end portion of the culture container 50, and the processes of step ST13 to step ST21 are repeated until the whole scanning is completed. Further, at a time point when the observation region R reaches the position of the scanning end point E shown in FIG. 13, the whole scanning ends (step ST22; YES).

After the whole scanning ends, the display controller 24 combines the phase difference images in the respective observation regions R to generate a composite phase difference image, and causes the display device 26 to display the generated composite phase difference image (step ST23).

As described above, in the present embodiment, an imaging position of an image of the observation target is adjusted on the basis of the adjustment value C0 according to the position of the culture container 50 in the vertical direction, detected by the detection section 18. Here, the first temperature T1 that is the temperature of the support members 30a and 30b that support the detection section 18 and the second temperature T2 that is the temperature of the support member 31 that supports the objective lens 14b are measured, and the third temperature T2 that is the temperature of the culture container 50 is measured. Then, the standard adjustment value Cb is corrected on the basis of the refractive index of the culture container 50 according to the first temperature T1, the second temperature T2, and the third temperature T3, the position of the objective lens 14b in the Z direction is moved on the basis of the corrected adjustment value C0, and then, the auto-focus control is performed. Thus, the imaging position of the image of the observation target is adjusted according to the positions of the detection section 18 and the imaging optical system 14 according to the temperatures, and the refractive index of the culture container 50 according to the temperatures. Accordingly, according to the present embodiment, it is possible to acquire a phase difference image with reduced blur even in a case where an ambient temperature is changed.

In the above-described embodiments, the temperatures are measured whenever the phase difference image is captured, but the imaging time of the culture container 50 is not so long, and thus, there is a case where the temperatures during imaging may be considered to be constant. In such a case, it is preferable to measure the first to third temperatures T1 to T3 before the start of imaging, to derive the correction coefficients k1 to k3 in the correction section 22, and to store the result in the storage section 25. Thus, it is not necessary to measure the first to third temperatures T1 to T3, and to derive the correction coefficients k1 to k3 whenever the position information is detected.

Figure 18:
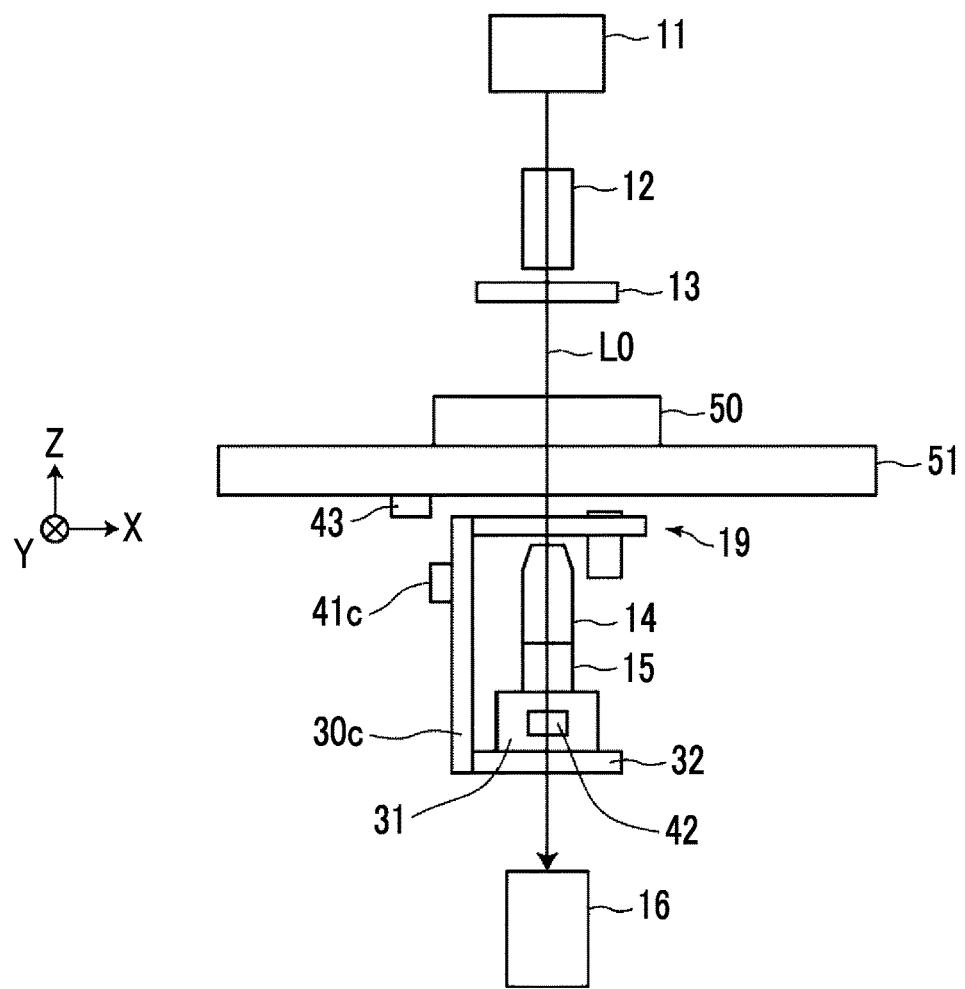
FIG. 18 is a block diagram showing a schematic configuration of a microscope observation system that uses an observation device according to a second embodiment of the present disclosure.

Hereinafter, a microscope observation system according to a second embodiment of the present disclosure will be described in detail with reference to the accompanying drawings. FIG. 18 is a diagram showing a schematic configuration of the microscope observation system according to the second embodiment. The microscope observation system of the second embodiment has a configuration of a detection section different from that of the microscope observation system of the first embodiment. Since the other configurations of the microscope observation system of the second embodiment are the same as in the first embodiment, the configuration of the detection section of the microscope observation system of the second embodiment will be mainly described below.

The detection section 18 of the first embodiment includes two displacement sensors 18a and 18b, and is configured to switch the displacement sensors 18a and 18b to be used according to a change in the movement direction of the observation region R, but a detection section 19 of the second embodiment includes one displacement sensor, and is configured to switch the position of the displacement sensor according to a change in the movement direction of the observation region R. In the second embodiment, the detection section 19 is supported by a support member 30c. Further, the temperature of the support member 30c is detected as a first temperature T1 by a temperature sensor 41c.

Figure 19:
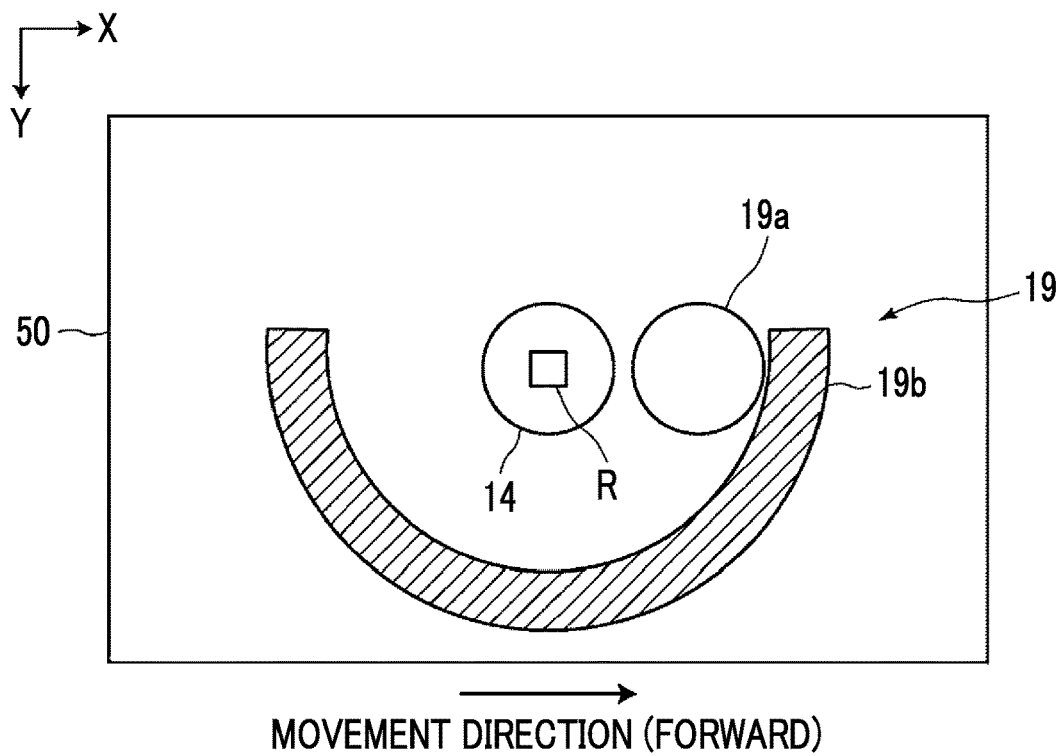
FIG. 19 is a diagram showing a configuration of a detection section of the observation device according to the second embodiment of the present disclosure.
Figure 20:
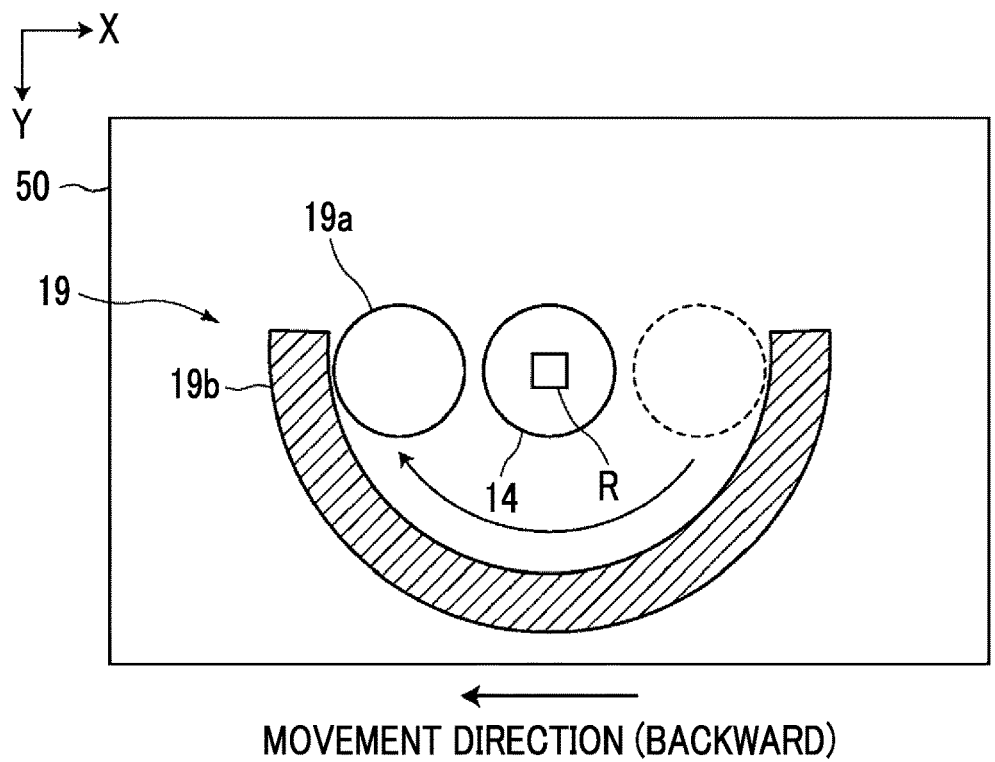
FIG. 20 is a diagram for illustrating position switching of a displacement sensor in the detection section of the observation device according to the second embodiment of the present disclosure.

FIGS. 19 and 20 are diagrams showing a specific configuration of the detection section 19. As shown in FIGS. 19 and 20, the detection section 19 includes a displacement sensor 19a and a guide mechanism 19b that guides the displacement sensor 19a to move its position.

The displacement sensor 19a is configured of a laser displacement sensor, similar to the first and second displacement sensors 18a and 18b of the first embodiment.

The guide mechanism 19b includes a semicircular guide member, and moves the displacement sensor 19a along the guide member. The guide member moves the displacement sensor 19a from one side to the other side in the X direction with the imaging optical system 14 being interposed therebetween.

FIG. 19 is a diagram showing the position of the displacement sensor 19a in a case where the movement direction of the observation region R is an arrow direction of FIG. 19 (a rightward direction of FIG. 19). On the other hand, FIG. 20 is a diagram showing the position of the displacement sensor 19a in a case where the movement direction of the observation region R is an arrow direction of FIG. 20 (a leftward direction of FIG. 20). In a case where the movement direction of the observation region R is changed from the arrow direction of FIG. 19 to the arrow direction of FIG. 20, the displacement sensor 19a moves from the position shown in FIG. 19 along the guide member of the guide mechanism 19b, and is switched to the position shown in FIG. 20.

In the present embodiment, the above-described guide mechanism 19b is provided as a displacement sensor moving mechanism for moving the position of the displacement sensor 19a, but the configuration of the displacement sensor moving mechanism is not limited thereto, and other configurations may be used as long as the position of the displacement sensor 19a can be changed in the same manner.

Other configurations and operations of the microscope observation system of the second embodiment are the same as those of the microscope observation system of the first embodiment.

Figure 21:
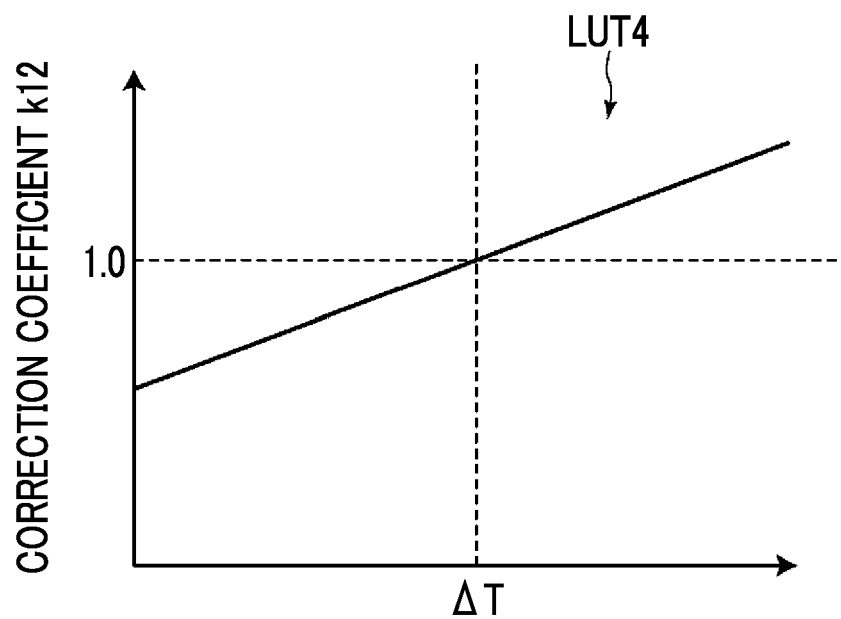
FIG. 21 is a diagram showing a relationship between a difference value between a first temperature and a second temperature and a correction coefficient.

In the above embodiment, the correction coefficients k1 and k2 are derived from the first temperature T1 of the support members 30a and 30b measured by the first temperature sensors 41a and 41b, and the second temperature T2 of the support member 31 measured by the second temperature sensor 42, respectively, to correct the standard adjustment value Cb. However, the standard adjustment value Cb may be corrected on the basis of a difference value between the first temperature T1 and the second temperature T2. In this case, as shown in FIG. 21, a relationship between a difference value ΔT between the first temperature T1 and the second temperature T2 and a correction coefficient k12 with respect to the standard adjustment value Cb is stored in the storage section 25 as a lookup table LUT4. Then, the correction section 22 calculates the difference value ΔT between the first temperature T1 and the second temperature T2, and derives the correction coefficient k12 with reference to the lookup table LUT4. In this case, the correction section 22 may derive the adjustment value C0 by correcting the standard adjustment value Cb using the correction coefficient k12 and the correction coefficient k3 by the following equation (4). The lookup table LUT4 may be obtained from a relationship between the lookup table LUT1 and the lookup table LUT2. In FIG. 21, as the difference value ΔT becomes larger, the value of the correction coefficient k12 becomes larger, but as the difference value ΔT becomes larger, the value of the correction coefficient k12 may be configured to become smaller.

$$C0 = Cb \cdot k12 \cdot k3 \quad (4)$$

Further, in the above embodiments, various lookup tables are shown in FIGS. 5 to 7, 12, and 21, but these lookup tables are only examples. According to properties (materials, sizes, temperature characteristics, or the like) of the objective lens 14b, the displacement sensor 18a and 18b, the culture container 50, the support members 30a and 30b of the displacement sensor 18a and 18b, and the support member 31 of the objective lens 14b, the characteristics of the lookup table are changed.

Further, in the above-described embodiments, the observation region R is moved by moving the stage 51, but the present disclosure is not limited thereto. A configuration in which the stage 51 is fixed and the imaging optical system 14 is moved to move the observation region R, so that the scanning based on the observation region R of the culture container 50 is performed, may be used, or a configuration in which both the stage 51 and the imaging optical system 14 are moved, so that the scanning based on the observation region R of the culture container 50 is performed, may be used.

Further, in the above-described embodiments, the present disclosure is applied to the phase difference microscope, but the present disclosure is not limited to the phase difference microscope, and may be applied to a different microscope such as a differential interference microscope or a bright field microscope.

In addition, in the above-described embodiments, a configuration in which a phase difference image formed by the imaging optical system 14 is captured by the imaging element 16 is shown, but a configuration in which an imaging element is not provided and an observation optical system or the like is provided so that a user is able to directly observe a phase difference image of an observation target formed by the imaging optical system 14 may be used.

Further, in the above-described embodiments, for example, as a hardware structure of processing units that execute various processes, such as the imaging optical system controller 21, the correction section 22, the scanning controller 23, and the display controller 24, the following various processors may be used. As described above, the various processors include a CPU that is a general-purpose processor that executes software (program) and functions as various processing units; a programmable logic device (PLD) that is a processor whose configuration is changeable after manufacturing, such as a field programmable gate array (FPGA), a dedicated electric circuit that is a processor having a circuit configuration dedicatedly designed to execute a specific process, such as an application specific integrated circuit (ASIC), or the like.

One processing unit may be configured by one of these various processors, or may be configured by a combination of two or more processors of the same type or different types (for example, a combination of a plurality of FPGAs or a combination of a CPU and an FPGA). Further, the plurality of processing units may be configured by one processor.

As an example in which a plurality of processing units is configured by one processor, first, as represented by a computer such as a client, a server, or the like, there is a form in which one processor is configured by a combination of one or more CPUs and software and one processor functions as a plurality of processing units. Second, as represented by a system on chip (SoC), or the like, there is a form in which a processor that realizes entire functions of a system including a plurality of processing units by one integrated circuit (IC) chip is used. As described above, the various processing units are configured using one or more of the various processors described above as a hardware structure.

Further, as the hardware structure of these various processors, more specifically, an electric circuitry in which circuit elements such as semiconductor elements are combined may be used.

EXPLANATION OF REFERENCES

10: microscope device
11: white light source
12: condenser lens
13: slit plate
14: imaging optical system
14a: phase difference lens
14b: objective lens
14c: phase plate
14d: imaging lens
15: imaging position adjustment section
16: imaging element
17: horizontal driving section
18: detection section
18a: first displacement sensor
18b: second displacement sensor
19: detection section
19a: displacement sensor
19b: guide mechanism
20: microscope control device
21: imaging optical system controller
22: correction section
23: scanning controller
24: display controller
25: storage section
26: display device
27: input device
30a, 30b, 30c, 31: support member
32: base
41a, 41b, 41c, 42, 43: temperature sensor
50: culture container
51: stage
51a: opening
60: scanning position in observation region
Cb: standard adjustment value
d1, D: apparent thickness of bottom portion of culture container
d2: thickness of bottom portion of culture container
E: scanning end point
f: focal length
k1 to k3, k12: correction coefficient
L0: illumination light
L1: laser light
LUT0 to LUT4: lookup table
M1: bottom surface of culture container
M2: lowest surface of culture container
S: scanning start point
t: thickness correction coefficient
T1: first temperature
T2: second temperature
T3: third temperature
V0: standard voltage
W: well
X0: optical axis
X1: normal line

What is claimed is:
1. An observation device comprising:
an imaging optical system that forms an image of an observation target contained in a transparent container;

a horizontal driving section that moves at least one of the container or the imaging optical system in a horizontal plane;

a scanning controller that controls the horizontal driving section to move an observation region of the imaging optical system and to scan the container;

a detection section that has at least one displacement sensor detecting a position of the container in a vertical direction, and detects the position of the container in the vertical direction at a position in front of a position of the observation region of the imaging optical system with respect to the container in a movement direction of the observation region;

an imaging position adjustment section that adjusts an imaging position of the image of the observation target on the basis of an adjustment value according to the position of the container in the vertical direction, detected by the detection section;

a first temperature measuring section that measures a temperature of a support member that supports the detection section as a first temperature;

a second temperature measuring section that measures a temperature of a support member that supports the imaging optical system as a second temperature;

a third temperature measuring section that measures a temperature of the container as a third temperature; and a correction section that corrects the adjustment value on the basis of a refractive index of the container according to the first temperature, the second temperature, and the third temperature, wherein the imaging position adjustment section adjusts the imaging position of the image of the observation target on the basis of the corrected adjustment value.

2. The observation device according to claim 1,
wherein the detection section switches a position of the displacement sensor or the displacement sensor to be used according to a change in the movement direction of the observation region.

3. The observation device according to claim 2,
wherein the container is a well plate having a plurality of wells,
the third temperature measuring section measures a temperature of each of the plurality of wells, and
the correction section corrects the adjustment value according to each of the plurality of wells.

4. The observation device according to claim 3,
wherein the imaging optical system includes an objective lens that forms the image of the observation target in the container,
the imaging position adjustment section adjusts the imaging position of the image of the observation target by adjusting a position of the objective lens in a vertical direction, and
the second temperature measuring section measures a temperature of a support member that supports the imaging position adjustment section.

5. The observation device according to claim 4,
wherein the correction section corrects the adjustment value on the basis of a temperature difference between the first temperature and the second temperature.

6. The observation device according to claim 2,
wherein the imaging optical system includes an objective lens that forms the image of the observation target in the container, the imaging position adjustment section adjusts the imaging position of the image of the observation target by adjusting a position of the objective lens in a vertical direction, and the second temperature measuring section measures a temperature of a support member that supports the imaging position adjustment section.

7. The observation device according to claim 6,
wherein the correction section corrects the adjustment value on the basis of a temperature difference between the first temperature and the second temperature.

8. The observation device according to claim 1,
wherein the container is a well plate having a plurality of wells,
the third temperature measuring section measures a temperature of each of the plurality of wells, and
the correction section corrects the adjustment value according to each of the plurality of wells.

9. The observation device according to claim 8,
wherein the imaging optical system includes an objective lens that forms the image of the observation target in the container,
the imaging position adjustment section adjusts the imaging position of the image of the observation target by adjusting a position of the objective lens in a vertical direction, and
the second temperature measuring section measures a temperature of a support member that supports the imaging position adjustment section.

10. The observation device according to claim 9,
wherein the correction section corrects the adjustment value on the basis of a temperature difference between the first temperature and the second temperature.

11. The observation device according to claim 1,
wherein the imaging optical system includes an objective lens that forms the image of the observation target in the container,
the imaging position adjustment section adjusts the imaging position of the image of the observation target by adjusting a position of the objective lens in a vertical direction, and
the second temperature measuring section measures a temperature of a support member that supports the imaging position adjustment section.

12. The observation device according to claim 11,
wherein the correction section corrects the adjustment value on the basis of a temperature difference between the first temperature and the second temperature.

13. The observation device according to claim 1,
wherein the correction section derives, with reference to a first lookup table that defines a relationship between the first temperature and a first correction coefficient for correcting the adjustment value, a second lookup table that defines a relationship between the second temperature and a second correction coefficient for correcting the adjustment value, and a third lookup table that defines a relationship between the third temperature and a third correction coefficient for correcting the adjustment value in consideration of the refractive index of the container according to the third temperature, the first correction coefficient, the second correction coefficient, and the third correction coefficient, and corrects the adjustment value by using the first correction coefficient, the second correction coefficient, and the third correction coefficient.

14. An observation method for moving at least one of a transparent container in which an observation target is contained or an imaging optical system that forms an image of the observation target in the container in a horizontal plane and capturing the image of the observation target formed by the imaging optical system using an imaging element, the method comprising:
- a step of including at least one displacement sensor detecting a position of the container in a vertical direction, and detecting the position of the container in the vertical direction at a position in front of a position of the observation region of the imaging optical system with respect to the container in a movement direction of the observation region, by a detection section that detects the position of the container in the vertical direction;
- a step of adjusting an imaging position of the image of the observation target on the basis of an adjustment value according to the position of the container in the vertical direction, detected by the detection section;
- a step of measuring a temperature of a support member that supports the detection section as a first temperature;
- a step of measuring a temperature of a support member that supports the imaging optical system as a second temperature;
- a step of measuring a temperature of the container as a third temperature; and
- a step of correcting the adjustment value on the basis of a refractive index of the container according to the first temperature, the second temperature, and the third temperature,
- wherein in the step of adjusting the imaging position, the imaging position of the image of the observation target is adjusted by the corrected adjustment value.

15. A non-transitory computer readable recording medium storing an observation device control program causing a computer to execute a procedure of moving at least one of a transparent container in which an observation target is contained or an imaging optical system that forms an image of the observation target in the container in a horizontal plane and capturing the image of the observation target formed by the imaging optical system using an imaging element, the program causing the computer to execute:
- a procedure of including at least one displacement sensor detecting a position of the container in a vertical direction, and detecting the position of the container in the vertical direction at a position in front of a position of the observation region of the imaging optical system with respect to the container in a movement direction of the observation region, by a detection section that detects the position of the container in the vertical direction;
- a procedure of adjusting an imaging position of the image of the observation target on the basis of an adjustment value according to the position of the container in the vertical direction detected by the detection section;
- a procedure of measuring a temperature of a support member that supports the detection section as a first temperature;
- a procedure of measuring a temperature of a support member that supports the imaging optical system as a second temperature;
- a procedure of measuring a temperature of the container as a third temperature; and
- a procedure of correcting the adjustment value on the basis of a refractive index of the container according to the first temperature, the second temperature, and the third temperature,
- wherein in the procedure of adjusting the imaging position, the imaging position of the image of the observation target is adjusted by the corrected adjustment value.

\* \* \* \* \*